United States Patent
Paulson et al.

(10) Patent No.: US 6,781,369 B2
(45) Date of Patent: Aug. 24, 2004

(54) ELECTROMAGNETIC ANALYSIS OF CONCRETE TENSIONING WIRES

(75) Inventors: Peter O. Paulson, Calgary (CA); John McIntyre, Calgary (CA); Kevin Mitchell, Calgary (CA)

(73) Assignee: Pure Technologies Ltd., Calgary (CA)

( * ) Notice: Subject to any disclaimer, the term of this patent is extended or adjusted under 35 U.S.C. 154(b) by 36 days.

(21) Appl. No.: 10/361,865

(22) Filed: Feb. 11, 2003

(65) Prior Publication Data

US 2003/0173959 A1 Sep. 18, 2003

Related U.S. Application Data

(62) Division of application No. 10/221,998, filed as application No. PCT/CA02/00085 on Jan. 29, 2002.

(30) Foreign Application Priority Data

| Jan. 29, 2001 | (CA) | 2332473 |
|---|---|---|
| Aug. 27, 2001 | (CA) | 2356239 |
| Nov. 15, 2001 | (CA) | 2361813 |

(51) Int. Cl.$^7$ .................. G01N 27/82; G01N 27/90
(52) U.S. Cl. ................... 324/220; 324/240
(58) Field of Search .................. 324/219, 220, 324/221, 228, 232, 235, 238, 242

(56) References Cited

U.S. PATENT DOCUMENTS

| 2,790,140 A | * | 4/1957 | Bender | 324/220 |
|---|---|---|---|---|
| 3,878,453 A | * | 4/1975 | Potter et al. | 324/326 |
| 5,027,285 A | * | 6/1991 | McCartney et al. | 702/58 |
| 5,068,608 A | * | 11/1991 | Clark, Jr. | 324/220 |
| 5,811,970 A | * | 9/1998 | Cook et al. | 324/233 |
| 5,821,747 A | * | 10/1998 | Atherton et al. | 324/220 |
| 6,127,823 A | * | 10/2000 | Atherton | 324/220 |
| 6,239,593 B1 | * | 5/2001 | Burkhardt et al. | 324/233 |

FOREIGN PATENT DOCUMENTS

| EP | 0529181 | 3/1993 |
|---|---|---|
| EP | 0580485 | 1/1994 |
| FR | 2766269 | 1/1999 |
| JP | 2000046802 | 2/2000 |
| JP | 2001349956 | 12/2001 |

OTHER PUBLICATIONS

"Inspection of non–piggable pipelines", JAN A de RAAD, Proc. of the 1995 Pipeline Pigging Conference, Feb. 13–16, 1995, Gulf Publishing Company ,pp. 1–12.
"Developments in Magnetic Inspection Techniques for Pipelines", David L. Atherton, J. Can Soc. NonDestructive Testing, vol. 11, No. 1 Jan/Feb, 1990, pp. 28–35.
"Investigations of the remote field eddy current technique in large diameter pipeline", David L. Atherton et al, Brit.J.NDT vol. 31, No. 9, Sep. 1989, pp. 485–488.
"Finite–Element calculations for shields in remote–field eddy current tools", David L. Atherton et al, Material Evaluation 47, Sep. 1989, pp. 1084–1088.

* cited by examiner

Primary Examiner—N. Le
Assistant Examiner—Darrell Kinder
(74) Attorney, Agent, or Firm—Blake, Cassels & Graydon LLP; Terry L. Leier

(57) ABSTRACT

Discloses methods to perform magnetic testing of tensioning elements in a pre-stressed concrete cylinder, such as a pipe or water reservoir and testing apparatus. The apparatus includes magnetic flux production means and detector means disposed proximal to a surface of the cylinder in a plane in common with the magnetic flux production means that is orthogonal to an axis of the cylinder. The apparatus operates over a range of low frequency signals, for example, between 20 and 300 hertz or a pulse. Output of the inspection apparatus includes a signal and distance plot showing the results of testing a cylinder at one or more frequencies. In accordance with another method of analysis, a characteristic of the phase of the output over distance is plotted, including the phase or representations of the in-phase or quadrature components of the received signal in relation to the driving signal.

30 Claims, 12 Drawing Sheets

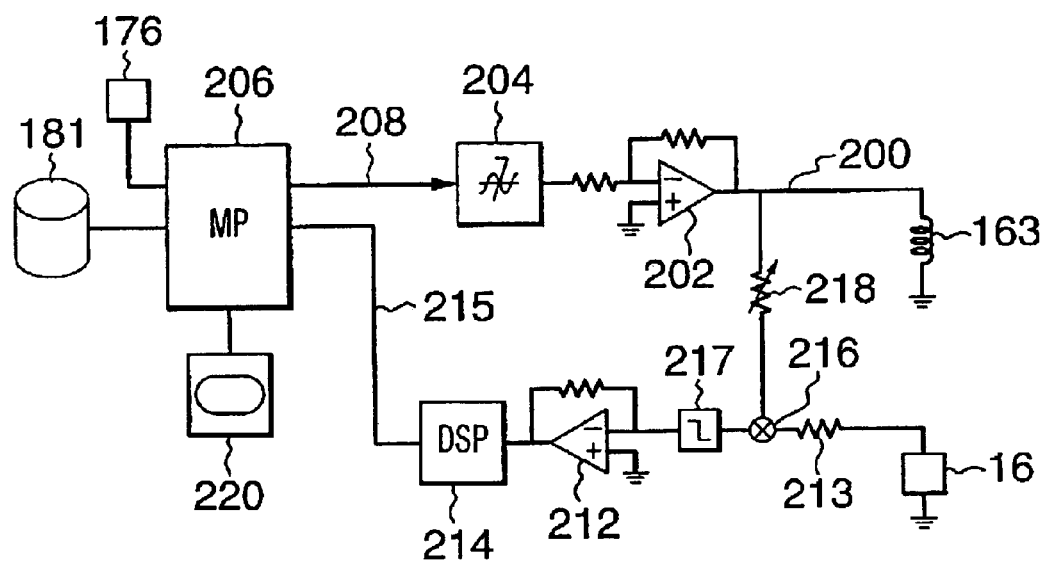
FIG. 7
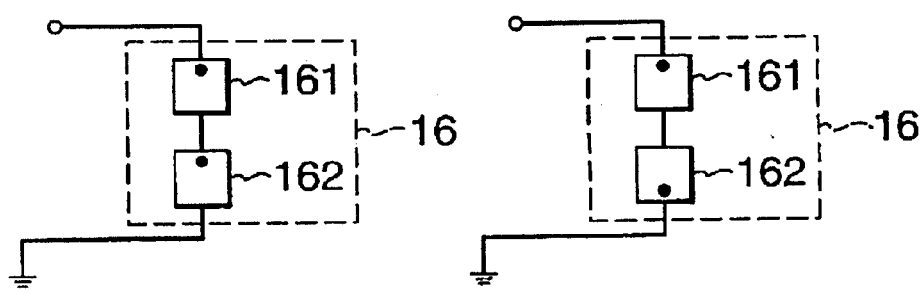
FIG. 7a   FIG. 7b

ELECTROMAGNETIC ANALYSIS OF CONCRETE TENSIONING WIRES

This is a divisional of co-pending application Ser. No. 10/221,998 filed on Jan. 07, 2003 which is a National Entry of International Application PCT/CA02/00085, filed on Jan. 29, 2002.

FIELD OF THE INVENTION

This invention relates to a method of non-destructive inspection of concrete conduits and cylinders, such as for example water pipes and water reservoir vessels, which are reinforced with metal wires. The invention also relates to apparatus for carrying out such inspections.

BACKGROUND OF THE INVENTION

There are many wire-reinforced concrete structures in use to contain or to conduct pressurized fluids, for example forming conduits in piping systems for water or forming water reservoir vessels. Typical concrete conduits are formed of concrete pressure pipe. Concrete pressure pipe consists of a thin steel cylinder, over which a layer of concrete is cast. Metal reinforcing wires are wound helically, either directly onto the metal cylinder or onto a layer of concrete cast on the cylinder. Often, a second layer of concrete is cast over the metal reinforcing wires. The exterior of the pipe is then finished with a layer of mortar.

Concrete vessels used for water storage (as for example to contain water for distribution) are usually cylindrical in cross-section, although they are occasionally oval in cross-section. The vessel is wrapped around its circumference with wire to provide compressive force to the concrete of the reservoir to support the water contained within the vessel forming the reservoir. Typically, the wire is of circular cross section, although other cross-sections (e.g. rectangular) are known as well.

The purpose of the reinforcing wires is to keep the concrete that they overlie in compression. Over time, the wires may corrode and eventually break. When this happens, it is possible that a rupture of the concrete conduit or reservoir vessel will occur, leading to escape of the pressurized fluid which it contains.

It is very expensive to replace an entire conduit or reservoir vessel. Therefore, it is preferred to carry on some sort of inspection procedure, to determine where wires have broken. This permits remedial work to be carried out only in locations that need it.

Prior techniques of inspection have not been completely successful. Some work has been done with remote eddy field current devices, and U.S. Pat. No. 6,127,823 of Atherton has proposed simultaneously using remote eddy field effects and transformer coupling effects for inspection. However, as admitted in that patent, the interpretation of the test results is complicated. Further, because the device of the Atherton patent preferably has a spacing of two to three pipe diameters between its exciter coil and its detector coil, it is not suited to detecting wire breaks near the ends of the pipeline, i.e. within two to three pipeline diameters of the end.

BRIEF DESCRIPTIONS OF THE INVENTION

According to the invention, an inspection device is provided for concrete pipes or vessels having a cylindrical wall reinforced with wires wound around the wall, or concrete vessels having an oval wall with wires wound around the wall. The device has one or more detectors proximal to the wall to be inspected. The detector can be inside or outside the wall. When the inspection device is used for inspecting pipelines, the detector is preferably inside the wall, attached to a vehicle which can be pulled through the pipeline.

In one embodiment, the detector is a coil having an axis parallel to the axis of the pipeline, and with an edge proximal to the wall of the pipeline. In a preferred embodiment, there are two detectors, axially spaced from each other. Preferably, where the detectors are coils, the detector coils have a diameter considerably less than the diameter of the pipeline being examined, and more preferably, not more than one-third of the diameter of the pipe being examined.

In another embodiment, the detector is a non-coil detector of electromagnetic fields, preferably a giant magneto resistive (GMR) sensor. Preferably, the detector comprises three GMR sensors, with their axes of sensitivity to magnetic flux orthogonal to one another. The magnetic flux in the direction desired to be measured (for example, along an axis parallel to the axis of a cylindrical pipeline or vessel) is measured by measuring the flux in the three orthogonal directions represented by the three detectors, and resolving the vectors to determine the flux in the desired direction.

In one manner of operation, the invention provides a driver coil to create an electromagnetic field, which creates a current flow through the wires forming part of the wire-wound concrete pipe or vessel. The voltage and other effects induced by this current in a detector are then measured.

Preferably, the driver coil has its axis orthogonal to the detectors, which may be radial to the pipe or vessel in one manner of orientation of the driver coil in relation to a cylindrical pipe or vessel being inspected. The axis of the driver coil will be discussed with relation to a cylindrical pipe or vessel, which is the normal case. If a pipe or vessel has an oval cross section, the two axes are parallel to one another. In that case, the term "the axis" used herein means either of the parallel axes.

It is preferred that the axis of the driver coil lies in a plane extending across the pipe or vessel, that is transverse to an axis of the pipe, and intersecting the detector. Where there are two detectors, the axis of the driver coil is preferably in a plane at right angles to an axis of the pipe and intermediate the two detectors. This has the advantage that there is no separation along the axis of the pipeline between the detector and the driver. This permits measurements to be taken up to only a few centimetres of the end of the pipe, which is not possible with apparatus where an axial separation must be maintained. Although not preferred, it is possible to use the invention with an axial separation along the pipe between the detector and the driver coil. Distances of up to 3.05 m. (10 feet) separation in a 6.1 m. (20 foot) diameter pipe have been found to work. However, such axial separation has no benefit, requires a longer mount for the equipment, and prevents taking readings near the ends of pipes.

In one embodiment, the detector is offset from the driver coil along an inner surface circumference of the pipe. The detector may be diametrically opposite the pipe from the driver coil. Where the detector is a coil, the axis of the detector coil is preferably parallel to the axis of the pipe. It is possible to have a driver coil that is not completely diametrically opposed to the detector, but it is preferred that the radius along which an axis of driver coil is, should at least be on a side of the central axis of the pipe that is remote from the detector. For large diameter pipes, such as 6.1 m. (20 foot) diameter pipes, it is preferable not to have the driver coil diametrically opposed from the detector, but circumferentially offset from it, to reduce the length of the equipment mounting boom on which the detector and driver coil are mounted.

In one method of operation, the invention provides a driver coil to create an electromagnetic field, which creates a current flow through the wires that wrap a concrete cylinder, such as a water reservoir or a very large diameter pipe. The voltage and other effects induced by this current in a detector located proximal to an exterior surface of the concrete cylinder remote from the driver coil are then measured.

The detector is remote from the driver coil along an outer surface circumference of the concrete cylinder. The detector may be diametrically opposite the cylinder under test from the driver coil. For large diameter cylinders, for example 6.1 m. (20 foot) diameter pipes or water reservoirs of even larger diameter, if the driver coil is not diametrically opposed from the detector, it is circumferentially offset from it. Where the detector is a coil, the axis of the detector coil is parallel to the axis of the cylinder under test.

There can be appreciable interference to the signal produced by the detector through direct magnetic flux coupling between the driver and the detector, for example, the magnetic flux formed within the pipe, between the detector and the driver. To counter this, it is preferable to orient the detector axis to be orthogonal to the driver axis. Further reduction of the direct magnetic flux coupling between the driver and the detector can be obtained by placing a substance of high permeability, which shields magnetic flux, in a position to block or substantially attenuate such magnetic flux. Mu-metal is a metal alloy that is expressly built to prevent passage of magnetic force, so a shield of mu-metal is preferred.

In a particularly preferred embodiment of the invention, a detector device according to the invention is mounted on a vehicle movable through the pipe. The vehicle is provided with a means for determining its location or distance of travel precisely. The vehicle proceeds down the pipe, while logging information from the magnetic pipe inspection and location or distance information. The location determination means provides a precise location, so that the information that is received about the state of the wires can be correlated to a particular location along the pipe. Optionally, the vehicle is also fitted with means to propel it through the pipe, and hydrophone means, which can carry out an acoustic examination of the walls as the vehicle is passing it through.

The vehicle is preferably sized so that, in a large pipeline, it can be placed in the pipeline through inspection ports, which are spaced along the pipeline. The vehicle can also be stopped at such inspection ports for the recharging of batteries and removal of recorded data. If desired, a whole or partial analysis can be done at the vehicle progresses through or traverses the pipe. The results can be displayed graphically to the operator. Alternatively, the data can be removed and analyzed at a remote location.

In one of its aspects, the invention provides an inspection apparatus for detecting discontinuities in spirally wound metallic wires embedded the wall of a concrete pipe, comprising a detector for producing an output responsive to a magnetic flux and a driver means to create magnetic flux and located not more than one pipe diameter along the axis of the pipe from the detector. Preferably, the detector is a coil oriented with an axis parallel to the concrete pipe, and the driver means is a coil with an axis orthogonal to the to the axis of the concrete pipe for inducing a current in the wires. The detector is oriented proximal to a surface of the pipe, preferably an inside surface.

In a preferred embodiment, the inspection apparatus includes displacement sensor means to produce an output representative of at least one distance of the detector a from a known location and means for causing the detector to move along a wall of such pipe as well as means for storing outputs corresponding to the flux detected by the detector and the displacement of the detector from such known location.

In another of its aspects, the invention provides a method of detecting discontinuities in spirally wound metallic wires reinforcing a concrete pipe, comprising providing a driving signal to a driver means having an axis oriented orthogonal to the axis of a concrete pipe and disposed proximal to an inside surface thereof to generate an induced current in said wires and providing a detector for producing an output responsive to a magnetic flux in a direction axial to said pipe, the detector being located in close proximity to an interior wall of a pipe and within one pipe diameter of the driver along the axis of the pipe. In accordance with the method, the detector is moved along the wall of the pipe, and the output and the location of the detector is recorded as it moves.

In another aspect, the invention provides a method of testing the spirally wound metallic wires reinforcing the wall of a concrete pipe, by generating a driving signal with a signal generator, providing a detector located in a fixed position relative to the signal generator and not more than one pipe diameter axially along the pipe therefrom, moving the detector and signal generator along the pipe, detecting a signal with said detector in response to said driving signal and determining the location along the pipe where the detector is located at the time each detected signal is detected. Preferably, the periodic driving signal is generated at more than one frequency, and the detector signal is recorded over a range of locations traversed along a length of pipe.

In another of its aspects, the invention provides a method for testing the spirally wound reinforcing wires embedded in the wall of a concrete pipe along a length thereof using apparatus including magnetic flux production means and magnetic flux detector means disposed proximal to a surface of the pipe, the magnetic flux production means and the magnetic flux detector means in a spaced relationship to the other and axially disposed within one pipe diameter to the other. The magnetic flux production means produces a magnetic field in response to a driving signal and the magnetic flux detector means produces a detector signal in response to magnetic flux, location indication means and control means operatively connected to said location indication means, to said magnetic flux means and to said detector means. The method comprises providing a driving signal of at least one frequency; receiving a detector signal; producing an output representative of the detector signal corresponding to the in-phase and quadrature components of the detector signal in relation to the driving signal; and recording the output representative of the detector signal and the location; whereby at least one output is recorded over a range of locations traversed along a length of pipe.

The invention will be further described with respect to the drawings, in which:

BRIEF DESCRIPTION OF THE DRAWINGS

FIG. 5b is a plot of voltage against distance using the detector of the invention, on the pipe of FIG. 5a.

FIG. 7 is functional schematic diagram of the electronic signal elements of an embodiment of the invention.

FIG. 7a is a functional schematic diagram of two sensors connected in a common polarity configuration.

FIG. 7b is a functional schematic diagram of two sensors connected in a reverse polarity configuration.

FIG. 15a is a cross section through a pre-stressed concrete pipe, showing schematically an alternate arrangement of the driver and detector around the pipe under test from the arrangement of FIG. 14a.

DETAILED DESCRIPTION OF THE INVENTION

Figure 1:
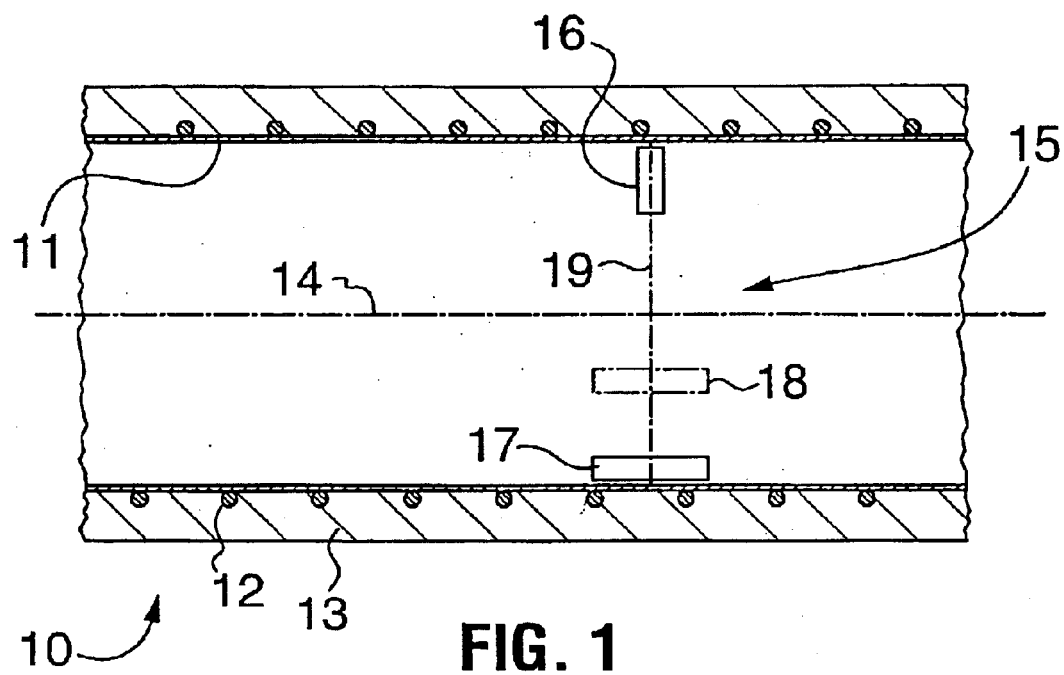
FIG. 1 is s cross-section through a pre-stressed concrete pipe, showing schematically a first form of detector according to the invention within such pipe.

The preferred embodiments of the invention will now be described with reference to the Figures. FIG. 1 shows a cross-section through a pre-stressed concrete pipe generally indicated as 10. A pre-stressed concrete pipe of this sort has an inner metal cylinder 11. Depending upon the type and grade of pipe, either pre-stressing wires are wound directly onto the cylinder, or a layer of concrete is cast onto the cylinder, and the pre-stressing wires are wound on the layer of concrete. Some pipes also have a layer of concrete cast inside the pipe, separating the metal cylinder from the interior. Other pipes have two layers of pre-stressing wires, with layers of concrete between them, outside the metal cylinder. Another layer of concrete or protective mortar is cast around the wires to complete the pipe. Pipes are sold under the designation ECP, LCP, SP5 and SP12, and are usually designed to meet AWWA standards C301 and C304. All of these types of concrete pressure pipe can be examined using the detector of the present invention.

In FIG. 1, pipe is shown as having a metal cylinder 11, wrapped with wires 12 embedded in concrete 13.

The pipe inspection apparatus is shown schematically at 15. The apparatus comprises a detector 16. This detector is preferably a coil detector capable of detecting magnetically induced fields or currents in the pipe being examined.

In the embodiment shown, the detector 16 is a coil, which is adapted to receive magnetic flux and convert it into a measurable electrical current and voltage. However, instead of a coil, any other detector of magnetic flux could be used. Another particularly preferred sensor is a giant magneto resistive sensor, or GMR sensor. Such sensors will be described henceforth in this application as "GMR sensors".

When detector 16 is a coil, it is located so that the axis of the coil is parallel to the centre axis 14 of the pipe. The detector 16 is placed so that it almost touches the wall of the pipe. It is preferred that the detector does not touch the wall, as this would impede movement of the detector along the interior surface of the wall. However, the gap between the detector 16 and wall of the pipe 10 should be kept as small as is conveniently possible, having regard for the fact that the detector is to be moved along the length of the pipe.

Reference numeral 19 represents a diameter of the pipe, which passes through detector 16. At the opposite end of the diameter 19 from detector 16, there is a driver coil 17. Preferably the driver coil is driven with low frequency alternating current, for example from 20 hertz to 300 hertz but may be driven with a pulse. The coil is located so that its axis is orthogonal to the axis of the pipe being inspected. The driver is placed by a wall of the pipe, and, in the preferred arrangement, it is preferable that the driver be disposed as close as possible to a wall of the pipe. Having regard to the fact that the apparatus will be moved along the pipe, it is not desirable to have the driver 17 drag against the wall of the pipe in operation of the apparatus.

Optionally, a shield 18 of a high permeability material, that is material that impedes the passage of magnetic flux therethrough, is placed between the detector 16 and the coil 17. A suitable material is mu-metal. The purpose of the mu-metal shield is to prevent magnetic flux passing through the contents of the pipeline directly to the detector 16 from the driver coil 17. It is intended that the primary signal picked up by the detector 16 should be the signal that is made by an induced current in the wires 12, because of the driver coil 17. A signal caused by magnetic flux in the contents of the pipeline would add noise to this signal. In a very large pipeline, particularly when the pipeline has been drained for inspection, the signal passing directly from the driver 17 to the detector 16 is often insignificant (large pipelines, for water transmission, are often several meters in diameter). However, where the pipeline is smaller, and particularly when the pipeline is filled with water, direct signals through the contents of the pipeline may be a problem, so the shield 18 is desirable in such circumstances. The desirability of the shield 18 can be determined by doing sample measurements with and without the shield, to see whether the shield makes an appreciable difference in the measurements.

Figure 2:
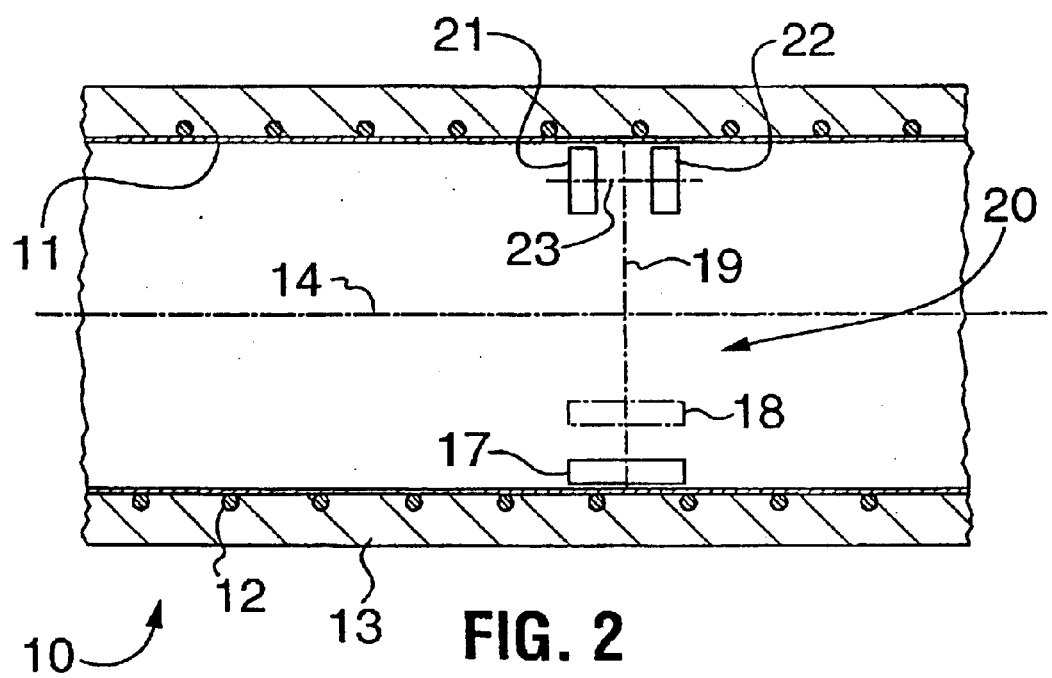
FIG. 2 is a cross-section of a similar pipe, showing a second embodiment of the inventive detector system.

FIG. 2 is a view similar to that of FIG. 1, showing a second embodiment of the inspection device. Reference numerals, where they are the same as used in FIG. 1, designate subject matter the same as in FIG. 1 in this and all subsequent figures.

In the embodiment of FIG. 2, the inspection device is generally shown as 20. It has detector means provided by two detectors 21 and 22, for example coils, which are spaced from one another along a common axis 23 by a distance less than the diameter 19 of the pipeline. Preferably, the spacing of the detectors is small, such as from about 7.5 centimetres to preferably not more than half the diameter of the pipeline.

Alternately, the detector means is a giant magnetoresistive (GMR) sensor which has an axis responsive to magnetic flux analogous to an axis of a coil detector. A GMR sensor provides an output which is a change in resistance that is induced in the GMR sensor by magnetic flux. To provide an analogous structure to the two detectors 21 and 21 of FIG. 3 or 3, the detector means is a pair of GMR and the output is a change in resistance induced in the GMR detects by magnetic flux.

Where it is desired to resolve a magnetic field in three dimensional space, three detectors oriented along each orthogonal axis can be used. For example, where the detector means has three detectors, each oriented to be responsive to a magnetic flux along a corresponding orthogonal axis.

Figure 3:
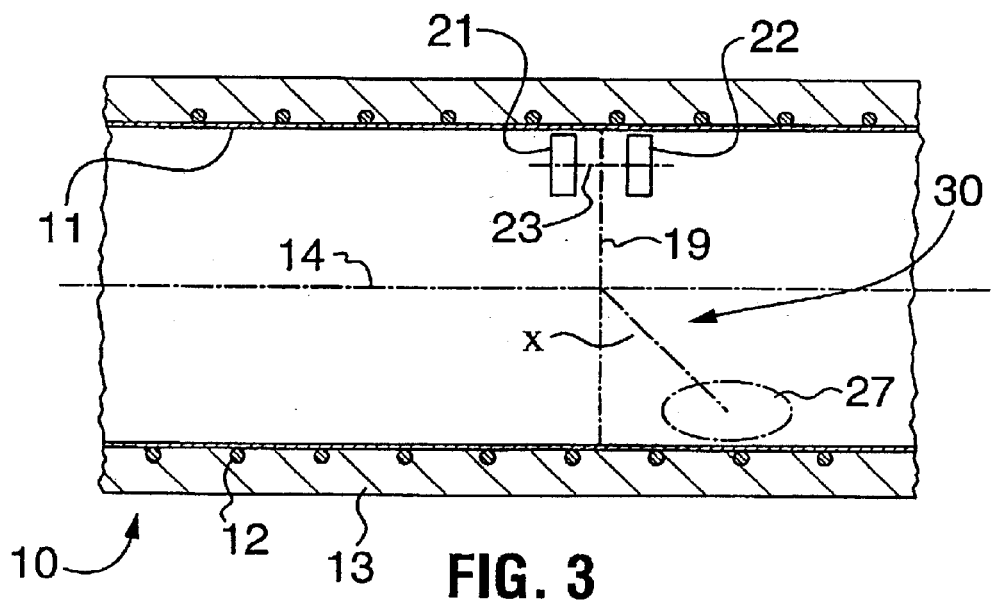
FIG. 3 is a cross-section through a similar pipe, showing a third embodiment of the inventive detector system.

In FIG. 3, the inspection device 30 has again two detectors 21 and 22 on a common axis 23. In this case however, there is a driver coil 27, which is not diametrically offset from the two detectors. The driver coil 27 can be located anywhere on the internal circumference of the pipeline, so long as it is far enough away so that the magnetic flux produced by current in the wires of the pipe are distinguishable from any stray magnetic fields from the driver coil. In this case, the driver coil is located approximately 45 degrees offset from the vertical diameter 19 across the pipe as shown by the angle x, and the coil is disposed radially of the pipe. Particularly in large pipes (for example the 20 foot (6.1 m.) diameter pipe mentioned above, it is preferable that the driver coil be offset from the vertical diameter, even if the driver coil is not axially offset along the pipe from the detector. The driver coil is offset circumferentially from the detector means by an angle x which preferably is at least 10 degrees. Where the driver coil is offset circumferentially from the detector means by an angle x, the circumferential offset is preferably a distance of at least one meter. This permits having a smaller set of booms on which to mount the detector and drive coil, and sometimes in large pipes results in a cleaner signal.

Figure 4:
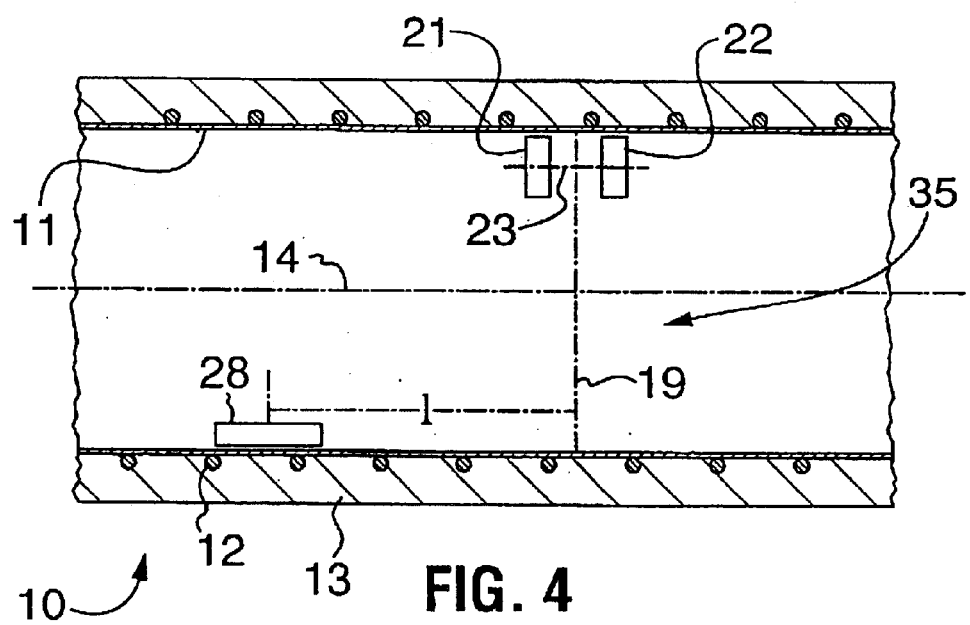
FIG. 4 is a cross-section through a similar pipe, showing a fourth embodiment of the detector system according to the invention.

FIG. 4 shows a detector with the same arrangement as FIG. 3. However, in FIG. 4 the detector has a driver coil, which is wrapped around an axis radial to the pipeline and spaced at a distance "I" from the diameter 19 between the detectors 21 and 22. The distance "I" is less than one pipeline diameter. Although not shown, magnetically impermeable barriers, such as barriers 18 in FIGS. 1 and 2, can be placed in the line of sight between driver coils 27 or 28 and detectors 21 and 22.

Generally, it is preferred not to offset, along the axis of the pipe, the driver coil from a line 19 extending orthogonal to the axis of the pipe to the detector coil or (in the case of two detector coils, a line located midway between the two detectors). If there is no offset of the driver relative to the detector, measurements can be made right to the end of a pipe section. Further, the signal detected is often clearer, with less "noise" as induced currents pass through fewer wires in the pipe before generating the major part of the magnetic flux proximal to the detector apparatus.

Figure 5A:
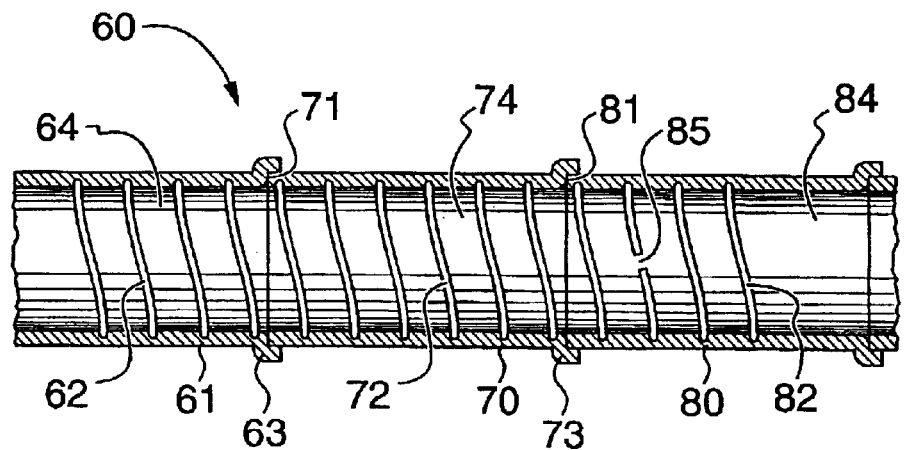
FIG. 5a is a schematic cross-section through a length of pipeline. In order to demonstrate a wire breakage, wires (which would in reality be concealed behind the metal lining in the view shown) are shown. Further, the drawing is not to scale, and dimensions have been distorted so that detail of wire placement and wire breaks can be shown.

FIG. 5a shows, in schematic form, a pipeline 60, having a series of pipes 61, 70 and 80. These are laid end to end to form the pipeline, and are connected by the well-known bell and spigot system. The pipeline is not shown to scale. Typically, the pipe sections would be of the order of three meters in length, and pipe diameters would be of the order of one and one half-two meters.

Pipe 61 is shown as joined to pipe 70 by a bell 63 which is part of pipe 61. A spigot 71 from pipe 70 is inserted into the bell, and suitably sealed. Similarly, pipe 70 has a bell 73, into which spigot 81 of pipe 80 is inserted and sealed. Each pipe is a concrete pressure pipe, having an internal metallic cylinder (numbered as 64 for pipe 61, 74 for pipe 70 and 84 for pipe 80). This is wrapped (either with or without an intervening layer of concrete as described) with helical reinforcing wire. For pipe 61, this wire is 62. For pipe 71, the wire is shown as 72 and for pipe 80, the wire is shown as 82. Only a very few wires schematically are shown for each pipe. In actual practice, the pipe would be closely wound with such wires, and there could be several layers of wire, separated by layers of concrete. The wires are overlaid with concrete or protective mortar to make the pipe.

In the drawing, a few selected wires are visible. In actual fact, these would not be seen in a cross-sectional view of the pipe, as the metal cylinders 64, 74 and 84 would hide them. However, they are shown for the purpose of illustrating what happens when there is a break. A break is shown in one wire at 85.

Figure 5B:
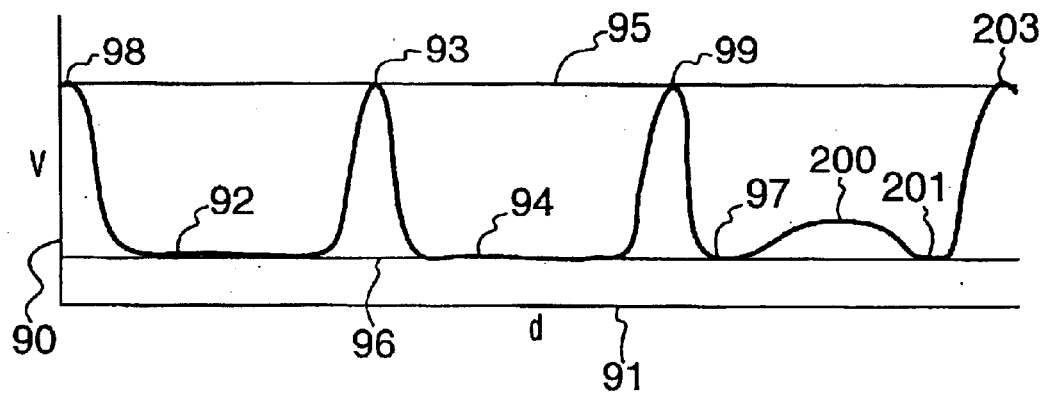

FIG. 5b is a plot of voltage against distance along the pipe, for one detector such as shown at 16 in FIG. 1. Driver coil 17 in FIG. 1 is generating a periodic signal at a selected frequency in the range frequency of 20–300 hertz, and detector 16 is receiving a voltage.

FIG. 5b shows a plot of this voltage against the distance travelled by detector 16 along the pipe. Detector 16 and driver coil 17 are rigidly linked, so that they each travel at the same speed.

FIG. 5b is a plot of voltage (on axis 90 of the plot) against distance travelled (on axis 91 of the plot). Only positive voltages are plotted on this plot. As will be seen, the pattern of the plot of voltage against distance is that there is a peak, as shown 93, as the detector traverses each of the bell and spigot connections. In between, there is a relatively flat portion. Thus, while the detector is traversing pipe 61, there is initially a peak 98 as the detector passes over the bell and spigot connection just before pipe 61, then a flat portion 92 as it traverses that pipe length. When it approaches bell and spigot connection 63, 71, the voltage rises again to a peak 93. After it has reversed that connection and is traversing pipe 70, the voltage again drops to a relatively flat portion 94.

After a series of pipes have been traversed, it becomes possible to determine an average voltage for the peak when a bell and spigot connection is passed. This average voltage is shown as 95. The voltage 95 is the average of peaks 98 and 93. Similarly, it is possible to predict an average voltage when the detector is passing over a section of the pipe that does not have a bell and spigot connection. This average voltage is shown as 96. In the example given, it is the average of the flat portions 92 and 94.

In the example given, as the detector 16 traverses the bell and spigot connection 73, 81, a further peak 99 is obtained in the voltage. This peak is approximately the same as peaks 98 and 93, as is expected from the previous peaks for bell and spigot connections. However, after dropping from peak 99, the voltage first drops approximately to average 96 as shown at 97, then rises again as shown at 200, then drops again as shown at 201 to approximately average 96, before rising again to another peak for a bell and spigot connection, as shown 203. The result is a "bulge" 200, which indicates that there is an anomaly in the pipe section being examined. This anomaly is indicative of a broken wire in pipe 80, as is shown in FIG. 5a at 85. (The drawings are not to scale).

When there is a single detector, it is possible to find the broken wire with a fair degree of accuracy, as being approximately at the midpoint of peak 200 in the curve of FIG. 5b. However, the accuracy can be greatly increased by using two sensors, as shown at 21 and 22 in FIG. 2. The two sensors (for example receiver coils) can be very close together (for example, about 0.6 cm apart) or can be spaced from each other by a longer distance, such as for example 60 cm. Generally, the total effect of the wire windings is symmetrical upstream and downstream of the detector coils. However, when there is a discontinuity in the helically wrapped wires, such as a wire break, this unbalances the effect, and a very large difference in the signal received at the two receiver coils is found. By analyzing the plots of the voltage against distance of the two coils, a very precise position can be given for the break in the wire.

Figure 5C:
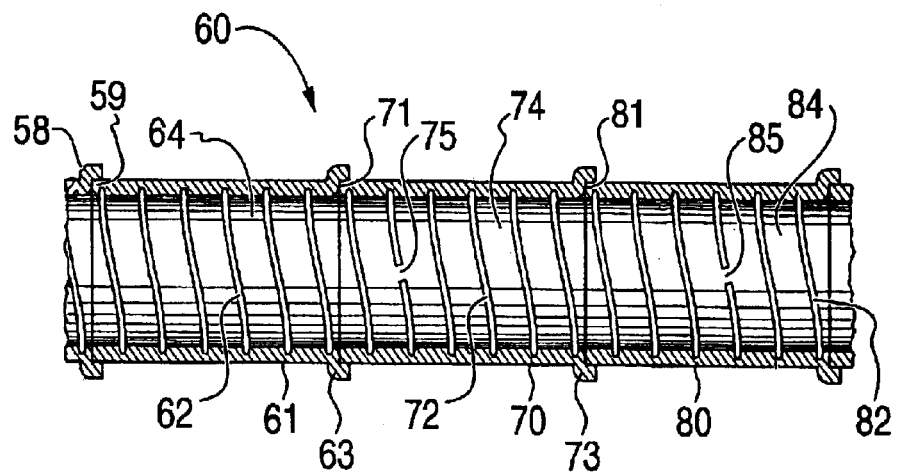
FIG. 5c is a schematic cross-section through a length of pipeline, which is not to scale and has distorted dimensions similar to FIG. 5a, with two wire breakages shown.

In FIG. 5c, a pipe section similar to that of FIG. 5a is shown. The same reference numerals are used to identify the same things. In this pipe, there are two broken wires at 75 and 85.

Figure 5D:
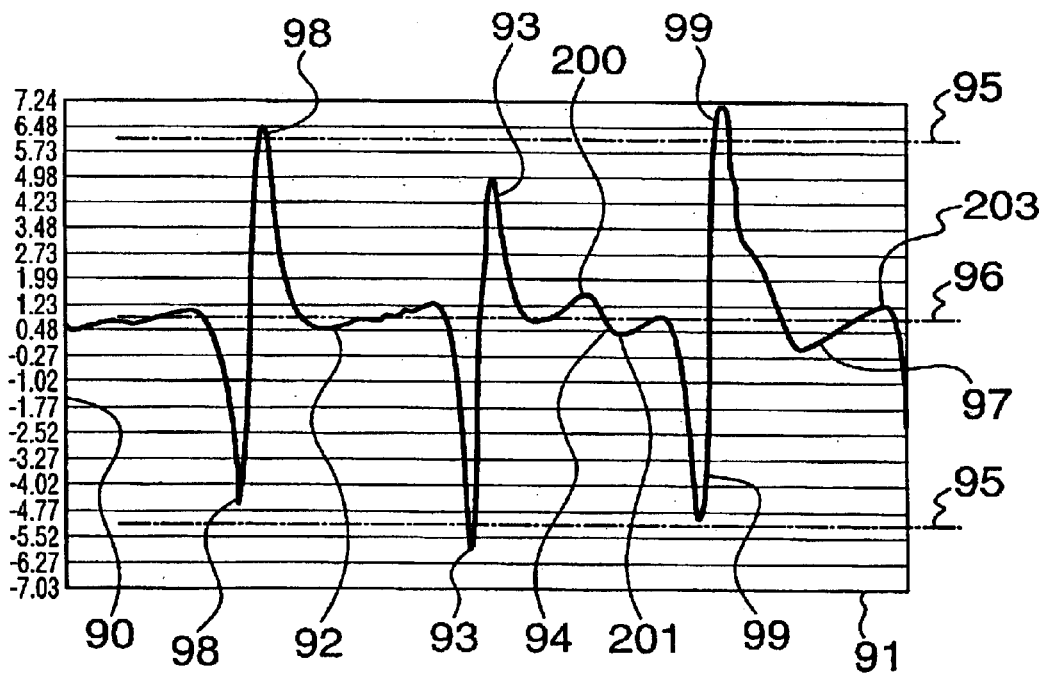
FIG. 5d is a plot representative of an output representative of the detector signal phase against distance produced in accordance with a method of the invention, from an inspection of the pipe of FIG. 5c.

FIG. 5d is a plot similar to that of FIG. 5c. However, the plot is produced from the phase relationship of the received signal to the driver signal which is represented as a phase angle, a voltage representative of the in-phase component of the received signal, a voltage, representative of the quadrature component of the received signal, or a voltage representative of either the in-phase or quadrature component of the received signal translated by a selected angle alpha, all of which are referred to herein as "the detector phase." A plot of the detector phase gives rise to peak and trough patterns, including positive and negative values, instead of the peaks shown in FIG. 5b.

As is shown in the plot, the pattern of the detector phase against distance is that there is an excursion resulting in peak-trough combinations at each of 98, 93 and 99 as the detector traverses each of the bell and spigot joint connections. In between, there is a relatively flat portion, which approximates the average 96 for the pipe portions between bell and spigot. Thus, while the detector completes traversing pipe 61, there is initially a diverging excursion resulting in peak and trough pair 98 as the detector passes over the bell and spigot connection 58, 59 on entering pipe 61, then a substantially flat portion 92 (approximating average 96) as it traverses the pipe length. When the detector approaches bell and spigot connection 63, 71, the plot makes a diverging excursion again to form peak and trough pair 93. After it has traversed that connection and is traversing pipe 70, the plot again drops to a flat region. However, in this case, the substantially flat region is interrupted by a small peak 200 and a small trough 201, which is a diverging excursion corresponding to wire break 75. When the detector approaches bell and spigot connection 73, 81, the plot makes a diverging excursion again to form peak and trough pair 99. After the detector has traversed that connection and is traversing pipe 80, the plot again drops. However, instead of reaching a substantially flat portion corresponding to line 96, it instead ramps down to a trough 97, and then rises to a small peak 203. The ramp and peak excursion corresponds to wire break 85.

After a series of pipes has been traversed, it becomes possible to determine an average of the upper and lower excursion of the peaks when a bell and spigot connection is passed. These averages are shown as upper and lower lines 95. Each of the upper and lower lines 95 is the average of the respective upper or lower peak excursions of the peak pairs, for example, 98, 93, and 99. Similarly, it is possible to predict an average signal when the detector is passing over a section of the pipe, which does not have a bell and spigot connection. This average is shown as 96.

Figure 6:
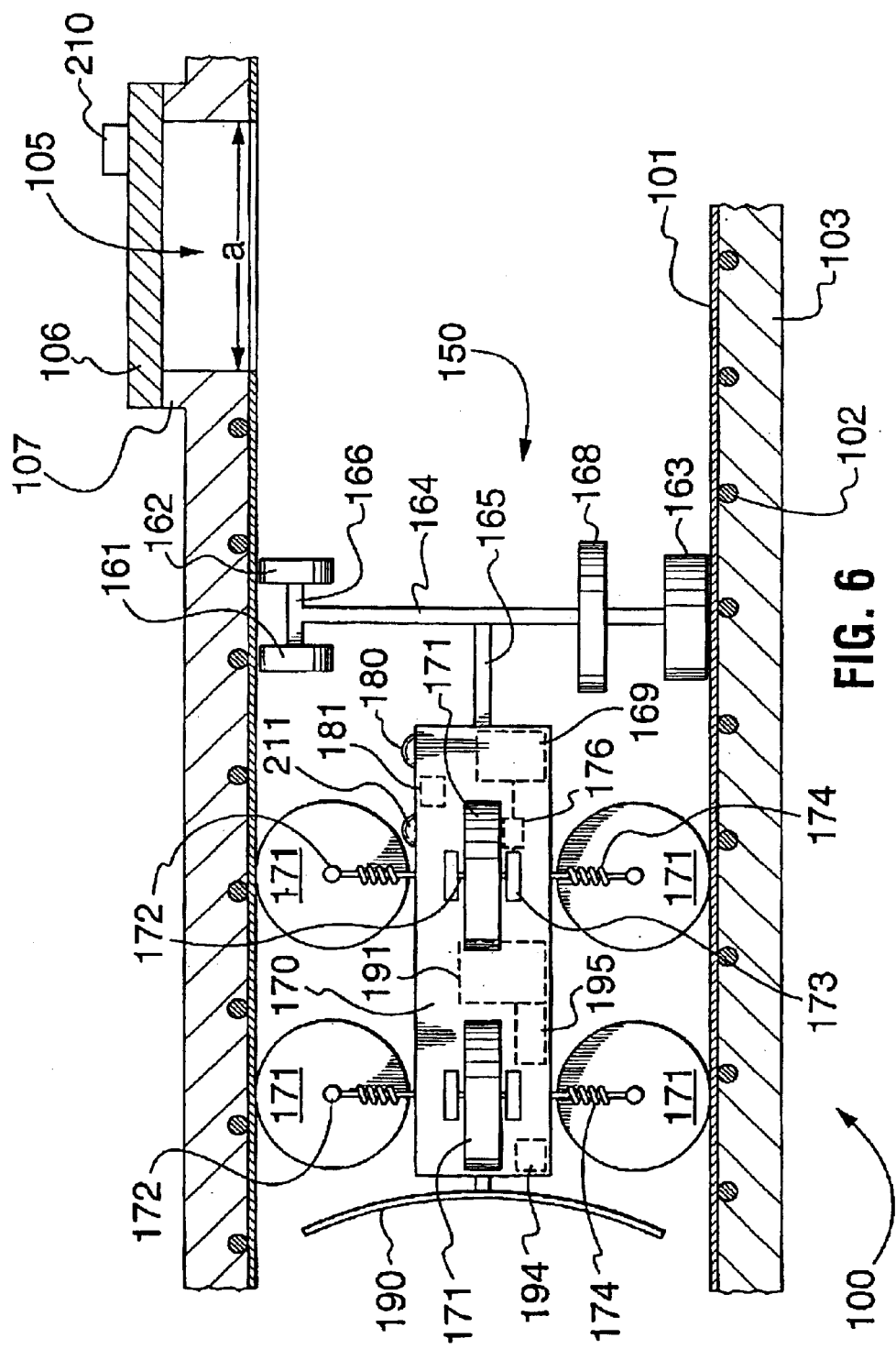
FIG. 6 is a vehicle designed to pass through a pipe according to the invention, and having a detector system according to the invention placed on it.

FIG. 6 shows a vehicle equipped with one embodiment of the apparatus of the invention (in this case the embodiment of FIG. 2). The vehicle is designed to pass through the pipelines to detect broken wires and other discontinuities. In FIG. 6, a concrete pipe is generally indicated as 100. The pipe 100 is formed of concrete 103 having helical wires 102 as reinforcement. Frequently, the pipe 100 has a steel cylinder 101 disposed interior to concrete 103 providing a steel-lined concrete pipe. Additional concrete lining may be provided interior to the steel cylinder 101. Although the pipe as shown in the figure does not have a concrete lining within the steel cylinder, the operation is the same when the pipe does have a concrete lining.

The pipe is provided at intervals with inspection hatches. Hatch 105 is one of such hatches. It has a flange 107, on which a hatch cover 106 rests removably. The hatch has an opening of a width shown by the arrow "a"

The inspection vehicle 150 has a body 170, with wheels 171. In the present embodiment, there are eight wheels extending outwardly along radii of the pipe spaced 90 degrees from each other, with two wheels 171 on each radius. Six of these wheels are shown in the drawing. Two others are behind the body 170. Each wheel 171 is on an axle 172, which is mounted to body 170 by means of a suitable axle support 173. Preferably the axle support 173 includes springs 174, so that the wheels will deflect from any discontinuity on the surface of the pipeline.

Extending from the front of the body 170 of the vehicle, in the direction that the vehicle will travel within a pipeline, is a support bar 165, which, as shown, is disposed axially of the pipeline. Connected to this at right angles is a frame 164, constructed from a non-ferromagnetic material such as aluminium or fibreglass to avoid a driver influence on the detector apparatus via the frame. Frame 164 has the detector apparatus mounted on an end remote from the driver 163. In the embodiment depicted, the detector apparatus is a pair of detectors 161 and 162 mounted on opposed ends of a crossbar 166. Preferably, the detectors are co-axial detector coils with their axis parallel to the central axis of the pipe. Alternately, the detectors are GMR sensors when GMR sensors are used, it is particularly preferred to have each detector made up of three GMR sensors with their axis of sensitivity orthogonal to one another, so as to detect the magnetic field from all directions. The two detectors 161 and 162 are spacedly disposed from each other approximately 10 cm apart. As discussed, the preferred spacing of the detectors can be from approximately 0.6 cm to 60 cm, depending on the size of the pipeline and precision desired. Each of the detectors 161 and 162 is responsive to a magnetic flux in its vicinity. For example, each detector is a coil which has a current induced in it by magnetic flux in its vicinity. Control means, generally referenced by block 169, are provided in the body of the vehicle to measure the current in each coil, and to record the current measured.

At the other end of frame 164 is a driver coil 163. This driver coil is driven by an alternating current in the 1–300 hertz range, or a pulse, of sufficient magnitude to induce a current flow in the wires of the pipe. A current source 191 is connected to driver coil 163 to provide the driving current. Magnetic barrier 168, preferably composed of mu-metal, is provided to block stray magnetic fields from extending through the volume enclosed by the pipeline between driver coil 163 and the detector apparatus, namely detectors 161 and 162.

A displacement sensor 176 to provide location information of the apparatus as it extends along the length of the pipe is provided, for example, an odometer. The displacement sensor 176 is connected to one of the wheels 171, to provide a displacement measurement based on the distance travelled by that wheel. Displacement sensor 176 produces a signal indicative of the distance travelled along the pipe, which is recorded with the recording of the outputs of detectors 161 and 162, to provide a record of distance travelled. Alternately, instead of being a displacement sensor, 176 can be a GPS locator or similar device that can determine and record its location.

The vehicle can be manually moved through the pipeline by being "walked" by an attendant, or it can be pulled through the pipeline by a wire line. However, it is especially preferred to have the vehicle autonomous. In this case, the vehicle can be placed in the pipeline at a point where there is a suitable opening. The vehicle is made so that it can be disassembled into parts, which can be handed into the pipeline through the inspection port 105 or similar ports. Thus, no single component of the vehicle has all of its dimensions greater than the distance represented by arrow "a". The result is that the vehicle can be passed into the pipeline in sections when the pipeline is depressurized, and can be assembled. Then, the operators can leave the pipeline and close off the inspection port, letting the vehicle remain in the pipeline.

If desired, the autonomous vehicle in the pipeline could have a motor means 195 sufficiently powerful to power it, either against or with the current of the pipeline (obviously, powering it with the current of the pipeline is preferable, as less power is required). If could also have battery means 194 to power this motor. However, it is preferred that the vehicle be carried along by the flow of the pipeline. In the present embodiment, there is a deflector 190 mounted on the back (i.e. upstream) end of the vehicle. When the flow of the fluid in the pipeline (usually water) hits the deflector, it pushes the device in a downstream direction (to the right in FIG. 6). An alternate way of propelling the device would be by deploying a parachute downstream (i.e. to the right of the device in FIG. 6) to pull it through the pipeline.

Suitably, the vehicle according to the invention can also be used to do other types of examination of the pipe as it passes through. For example, FIG. 6 shows hydrophone 180 mounted on body 170 of the vehicle. The hydrophone 180 senses sounds in the vicinity of the vehicle as it passes through the pipe. The data produced by hydrophone may be stored in a data storage device 181 along with location data produced by the displacement sensor 176. The hydrophone data can be used to indicate sites of possible leakage and other information as known in the hydrophone art. Other types of sensors can also be mounted on the machine.

The vehicle can also be equipped with automatic data transfer capabilities. Thus, as the vehicle approaches an inspection port 105, an operator can trigger it to transmit the data that it has received and an operator on the other side of inspection port 105 can operate a probe to receive this data by wireless modem, acoustic modem, or inductive coupling and/or recharge the batteries as needed. Alternately, as the vehicle reaches an inspection port, a barrier can be placed in the pipeline at the inspection port to stop the vehicle. The line can then be depressurized and the inspection port can be opened. The vehicle can then be examined for its physical condition, the data that it has collected can be downloaded, and the batteries, which provide the output generated by the AC current of the driver coil can be recharged.

It is also within the scope of the invention to provide motor means 195 and battery 194, for use if the vehicle becomes stuck between inspection stations, or if the current in the pipeline becomes insufficient to move it. If desired, this can be triggered by a sound signal of a predetermined sort, which can be sent from an inspection port 105 and received by hydrophone 180. There are of course other known means to control movement of the vehicle, as by having it drag a wire line.

The output signal from such a vehicle can be presented as a graph such as that shown in FIG. 5*b*. It is extremely easy to notice from such a graph where a wire break has occurred. It is also possible, however, to have initial processing done on the vehicle, so that the vehicle will prepare a supplementary data stream, which generates an exception when there is a voltage which is not at the voltage indicated as 95 or 96 in FIG. 5*b*, and which is not part of the smooth transition between them. Thus, the voltage registered at 200 would be noted as an exception. Thus, a signal would be generated showing each exception, together with the distance (according to the displacement sensor) at which the exception occurred.

It is within the invention to use other distance measuring means other than a displacement sensor 176 mounted on the vehicle. For example means for measuring the velocity of the vehicle and the time that it has moved at that velocity are suitable, particularly if there are calibrating means at inspection ports to provide a calibration as the vehicle passes. A location sensor such as a GPS sensor can also be used.

Suitably, the vehicle can also have a means to control its velocity when it is passing through the pipe. For example, the system can, when it does on site processing and indicates that there is an anomalous signal which could represent a wire break, have means to change the angle of deflector 190, so that it will move more slowly through the pipe for a predetermined distance thereafter. Alternately, the deflector can be adjusted so that the device will stop completely before a predetermined time, after which the deflector then is moved so that the vehicle will continue moving through the pipe. Other inspection means, for example hydrophone 180, can be used to provide acoustical signalling which can be utilized to determine if there is continued wire breakage occurring at or around a location where there is an anomalous signal.

In most pre-stressed water or sewage pipe, fluid flow within the pipe is one to ten feet per second. This is a very convenient speed at which to carry out inspection. Inspection with the autonomous vehicle of the invention permits the inspection to be done without interrupting flow or emptying the pipe.

The invention also comprises instrumentation exterior to the pipe (for example at access ports 105, which recognize signals emitted by the vehicle). For example, the vehicle can have a transponder 211, which responds to a sound emitted by a fixed location transponder 210, for example on access port 105, and responds with a sound of its own, thereby giving location information as it passes by inspection ports so equipped. This equipment can also be used for calibration of the distance measurement as discussed above.

It is preferred that attachments 164, 165 and 166 are provided with mechanical damping means, so that mechanical vibration is kept to a minimum, as such vibration can lead to electrical noise which could effect the quality of the signal being received.

FIG. 7 shows a functional schematic diagram of a circuit that can be used to implement the electronic components of the present invention. An output signal to drive the driver coil 163 of the invention is obtained from output line 200. An amplifier 202 provides sufficient signal power on output line 200 to produce a magnetic field from driver coil 163 that is efficacious for the purposes of the electromagnetic inspection of the present invention. An opamp is shown as the amplifier 202 in the functional schematic diagram. Power transistors or a more elaborate amplifier circuitry can be used to provide the amplifier 202 that will function to produce the signal power for output on output line 200. A variable frequency signal generator 204 provides a periodic signal for input to amplifier 202. Microprocessor 206 provides the parameters of the periodic signal. The parameters define the periodic signal produced, which is preferably, a sine wave, but can include, for example, a square wave or a sawtooth wave periodic signal. A sine wave is preferable as it provides a single frequency output signal. A pulse signal can also be used to obtain a transient response signal at the detectors. The type of the periodic signal and its repetition rate or frequency is set by microprocessor 206 over data communications line 208. In this arrangement, microprocessor 206 controls the parameters of the frequency and type of wave of the periodic signal that is to be produced by the variable frequency signal generator 204. The parameters may define a periodic signal that is a range of frequencies, for example, 20–300 Hz, which are to be continuously produced by the signal traversed over a given time period, such as a few seconds or milliseconds. Parameters defining this type of driving signal produce a continuous frequency sweep over the range of interest repeated for each successive time period.

Output from the detector apparatus 16 is received on input line 213 where it is supplied to an input of a multiplier 216. A reference signal derived from the output signal appearing on output line 200 is also supplied to an input of multiplier 216 via an attenuator 218. The output signal of the multiplier is low pass filtered at 217 and supplied to input amplifier 212. In this manner, the signal arriving at the input amplifier 212 is a signal that represents differences between the driver coil signal and the detector signal. The filtered signal output from multiplier 216 is amplified by input amplifier 212 and converted to a digital signal by a digital signal processor (DSP) 214. Thus the digital signal of DSP 214 is derived from the output of the sensor 16. While only one input line 213 and corresponding amplifier 212 and DSP 214 is shown in the diagram, an additional input line can be provided if desired. If there are two detectors, for example 161 and 162 as depicted in the other figures, and each is to provide an independent input to the microprocessor 206 for processing, then a second path, duplicating input line 213, multiplier 216, amplifier 212 and DSP 214 is provided. To use two detectors to provide a single input signal on input line 213, the output from detectors 161 and 162 is coupled together. The detectors can be coupled in a common polarity or a reverse polarity configuration. FIG. 7a shows the coupling of detectors 161 and 162 together in a common polarity configuration. In this configuration, the signal output of the detector apparatus is coupled in an additive fashion such that the sum of the outputs of each of the detectors 161 and 162 adds to the signal that is provided on input line 213. FIG. 7b shown the coupling of detectors 161 and 162 together in a reverse polarity configuration. In this configuration, the signal output of the detector apparatus is coupled in an subtractive fashion such that the difference of the outputs of each of the detectors 161 and 162 is the signal that is provided on input line 213. By using more than one detector, different locations and orientations of detectors can be achieved.

A displacement sensor 176 provides input to microprocessor 206 representative of the location of the vehicle in the pipe. When the apparatus of the present invention is placed in a pipe as depicted in FIG. 6, the magnetic coupling between driver coil 162 and the detector apparatus is manifested by variations in the input signal provided to amplifier 212. Microprocessor 206 receives digital signals representative of the input signal over data line 220 and performs computations based on the received digital signals to produce a visually perceptible output on display device 220. Preferably, the visually perceptible output is graph on a display device 220. Display device 220 can be a computer monitor such as a CRT or LCD, or, display 220 can be a printer that produces a printed output of the signal. The output produced may include processing performed on the signal, for example to provide numeric outputs as graph axis, produce averages traces or change trace colours. The signal received by the microprocessor 206 can be stored in a data storage device 181, which can be a magnetic disk or other suitable form of storage device such as, for example, a floppy disk or CD.

Because the output of detector 16 is subject to noise, it is preferable to use a phase sensitive detector, or a lock-in amplifier, on the detector output in place of multiplier 216 and amplifier 212. A phase sensitive detector multiplies the signal received from the detector with the reference, or transmitter, signal and integrates the resulting product signal to produce a DC signal representative of the amplitude of the received signal. A description of manner of operation and use of a phase sensitive detector and lock-in amplifier may be found, for example, in the publication DSP Lock-In Amplifier model SR830, Revision 1.5, November 1999 published by Stanford Research Systems of Sunnyvale Calif.

Figure 8:
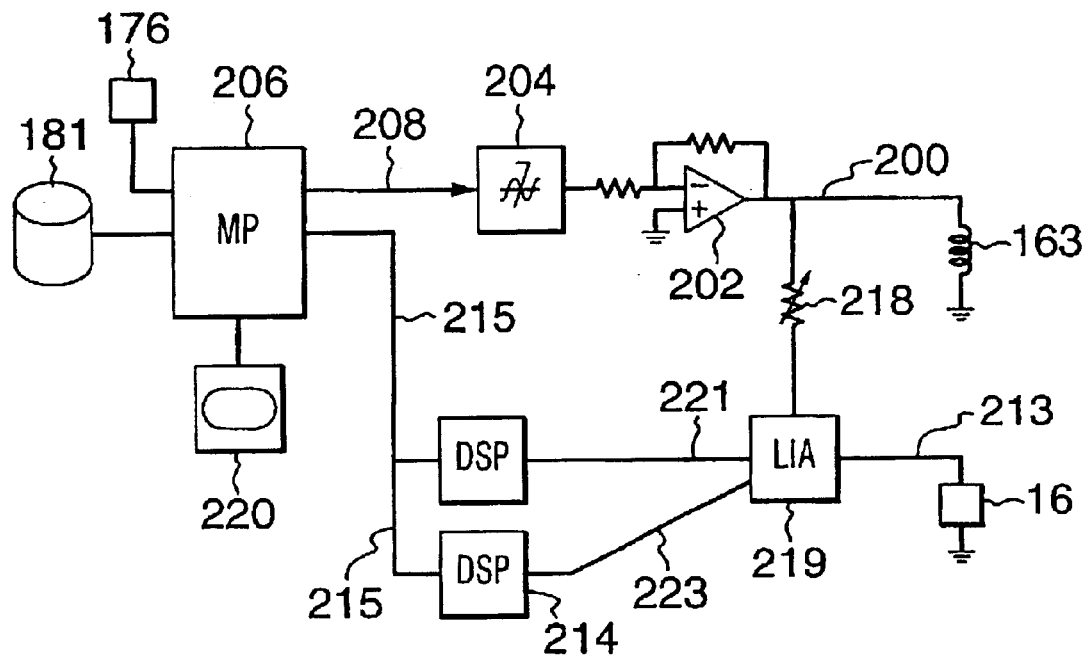
FIG. 8 is functional schematic diagram of the electronic signal elements of a preferred embodiment of the invention.

FIG. 8 shows a functional schematic diagram of a preferred embodiment of a circuit to implement the electronic components of the present invention. The driver configuration is a shown in FIG. 7, however, the input received from the detector apparatus 16 on line 213 is supplied to a lock-in amplifier, for example, a model SR830 manufactured by Stanford Research Systems of Sunnyvale, Calif. The type of periodic signal is preferably a sine wave, but can include, for example, a square wave or a sawtooth wave periodic signal. If other signals than a sine wave are used, the lock-in amplifier will provide an output reference only to the fundamental frequency of the periodic signal, the higher harmonic components will be discarded. Microprocessor 206 controls the parameters of the driving signal. For example, the sweep frequency range and time frame, or a frequency, the type of wave as parameters of the periodic signal that is to be produced by the variable frequency signal generator 204.

Figure 8A:
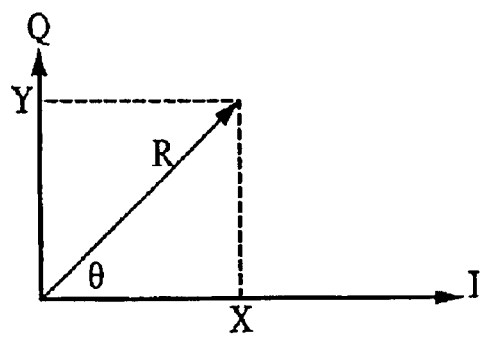
FIG. 8a is a graph of a vector output representing the in-phase and quadrature components of a received signal output from a lock-in amplifier.

FIG. 8a shows an output from the detector apparatus 16 is received on input line 213 where it is supplied to an input of lock-in amplifier (LIA) 219. A reference signal input to LIA 219 is derived from the output signal appearing on output line 200, which may be reduced in magnitude if needed by an attenuator 218. The LIA 219 provides two output signals on 221 and 223, which represent the magnitude and phase of the AC signal produced by detector 16 at the frequency corresponding to the reference frequency. The output on 221 and 223 can take either the form of an (X, Y) value pair as Cartesian co-ordinates, which define the in-phase (shown as X on the I axis) and quadrature (shown as Y on the Q axis) components of the received signal. The received signal may also be represented in polar co-ordinates as an (R, Theta) value pair. Using either co-ordinate method, the value pair defines a vector representative of the received signal in relation to the fundamental frequency of the driving signal.

The value pair produced by LIA 219 is converted to a digital form by DSP's 214 and supplied to microprocessor 206 where it is stored in storage 181. While only one input signal path comprising detector 16 and corresponding input line 213, LIA 219 and DSP's 214 are shown in the diagram, an additional input path can be provided for each additional detector. For example, if there are two detectors 161 and 162 as depicted in the other figures, and each is to provide an independent input signal to the microprocessor 206 for processing, then each detector would have a signal path comprising input line 213, LIA 219 and DSP's 214.

Figure 9:
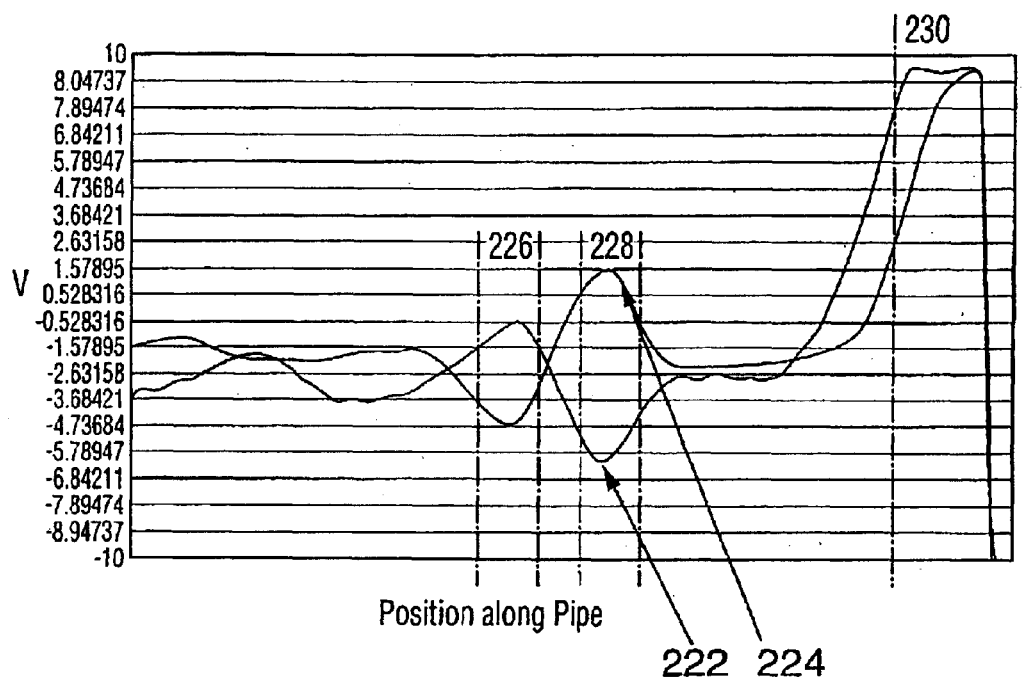
FIG. 9 is a graph showing detector trace plots produced in accordance with the invention for two exemplary driving frequencies.

FIG. 9 is a graph of an output provided on display 220. The detector apparatus produces an output signal while traversing a length of pipe, which is stored in storage 181. This data is used to produce the graph of FIG. 9. The graph provides the distance of travel of the detector apparatus along the length of the pipe is shown as the horizontal axis of the graph. The vertical axis of the graph represents a voltage level output of the LIA 219 output as received signal at DSP 214. The plotted voltage level, can be either the X component, that is the in-phase component of the received signal, output of LIA 219, or the Y component, that is the quadrature component of the received signal, output of LIA 219. The plot may be produced at the time the pipe is tested or may be produced at a subsequent time from the data stored in storage 181.

The plot of FIG. 9 is a plot produced from a multiple frequencies and provides a multi-frequency analysis of the pipe. In the plot of FIG. 9, the multi-frequency analysis is performed using two selected separate frequencies. Thus, there are two traces shown in the graph, each relating to a different frequency of a periodic signal output to the driver coil. Trace 222 is a trace produced at a first selected frequency and trace 224 is a second trace produced at a second selected frequency, which differs from the first frequency. The frequencies are chosen such that the slope of the traces produced by a broken wire shows a reversal when the same pipe section is surveyed by the two different frequencies but the traces produced by other features of the pipe do not result in a slope reversal. In the example of the graph of FIG. 9, the response represented by line 222 is a response corresponding to a sine wave driver signal at frequency of 85 Hz. The trace produced at 224 is the response corresponding to a sine wave driver signal at a frequency of 35 Hz.

The response of the detector is different at the two frequencies and the differences in the response produced by the detector apparatus at the two frequencies provides information to determine whether anomalies such as wire breaks are present in the helically extending tensioned wires 102 of the pipe. The frequencies depicted in the graph plots are selected from the range of frequencies at which the magnetic inspection test of the pipe was conducted. Naturally, the range of frequencies that a pipe was tested at may be many more than those that are subsequently used to produce a particular graph. The response to wire breaks shown in the region labelled 226 has a positive sloping excursion for the 222 trace and a negative slope extending excursion for the 224 trace. The reverse in sign of the slope at the differing frequencies provides an indication that a wire break is present in the region of 226. The response from wire breaks to frequencies, chosen in this way, results in a trace pair that has diverging excursion slopes where wire breaks exist, but non-diverging slopes where other features exist, such as pipe joints. The traces may form a mirror image excursion in the region of the anomaly as depicted in region 226 of the trace. The response in the region at 228 shows similar mirror image excursion and reversed sign slopes that indicate a wire break anomaly. The driver coil and detector are in a plane substantially orthogonal to the axis of the pipe under inspection. Region 230 of the graph of FIG. 8 shows a response when the detector passes through the region of a bell and spigot pipe joint, which provides a consistent excursion of the traces for each frequency. That is, the excursion slope of each trace has the same sign. Each has a positive sloping excursion, or each has a negative sloping excursion.

The response trace of the detector apparatus to a wire break provides a diverging signal response trace at selected different frequencies in the region when a wire break is located. However, when the detector passes over a pipe joint, the selected different frequencies produce excursions with each excursion having the same sign slope. In this manner, the driving signal frequencies can be used to produce traces that distinguish between wire breaks and pipe joints.

The manner of supplying differing frequency driving signals to perform a magnetic inspection test of a pipe can be achieved by several methods of operation of the inspection apparatus. In one method of operation, the detector apparatus is passed through the pipe to be inspected several times. Each pass has a different frequency that is tested. In a first pass a first driving frequency produces one trace, for example one of the traces appearing in the graph of FIG. 8. The detector apparatus is repositioned to the same start position and a second pass occurs at a frequency different than the first. In the example shown in FIG. 7 of the drawings, a first pass was made at 35 Hz, the vehicle was repositioned to the start position and a second pass was performed at the 85 Hz driver frequency.

Another manner of operating the apparatus is to perform a pass in each direction at a different frequency. In this manner of operation, a first pass along the pipe length occurs at a first frequency. When the end of the course of traverse of the pipeline that the inspection is to be performed for has been reached, the driving frequency is changed to the second desired frequency. From the end position, the detector apparatus moves in a reverse direction back toward the start point and detection is performed at a second driver frequency. In this manner, each traversal of the detector apparatus through the pipeline in either a forward direction or a reverse direction will produce a trace. Thus, in this manner of operation one half of the number of traversals is required than would be required by operating the apparatus in a forward direction only.

A third manner of operation of the detector apparatus is to advance the detector apparatus to discrete locations within the pipe. At each discrete location, the driver signal is swept over a range of frequencies or stepped through the various frequencies that are to be used in the pipe inspection. In this manner of operation, the detector apparatus is advanced incrementally and at each test location, the test frequency is to the desired settings. To produce the trace of FIG. 8 in this manner of operation, the detector apparatus is positioned at a first position. At that position, the variable frequency signal generator 204 is operated to produce a periodic signal at 35 Hz and the detector signal is captured. The periodic driving signal is set to the next frequency, 85 Hz, and the detector signal is then captured. When all of the periodic driving signal frequencies of interest have been produced at the position, the detector apparatus is then advanced to the next position. At the next location, the periodic driver signal frequency cycle is repeated. Operating the detector apparatus in this manner requires only a single traversal of the pipe section to be inspected. At the conclusion of the traversal, data points are collected to produce all of the traces representative of all the frequencies that the detection occurred at during the course of the traversal of the pipe.

A fourth method is to move the inspection apparatus through the pipe continuously while continuously changing the frequency of the driver apparatus. When the frequency of the driver apparatus is changed sufficiently rapidly relative to the velocity of the inspection apparatus, all of the frequencies of interest are applied every few inches of displacement along the pipe. Traces representing each individual component frequency of interest can be produced from data recorded during the inspection process. Thus, for example, the frequency can be varied continuously from 100 Hz to 200 Hz over a period of 1 second and data can be recovered at a sampling rate of 15,000 points per second. The when it is desired to view the results at a particular frequency, the sampling points that were captured at that frequency or the closest available frequency can be viewed.

Figure 10:
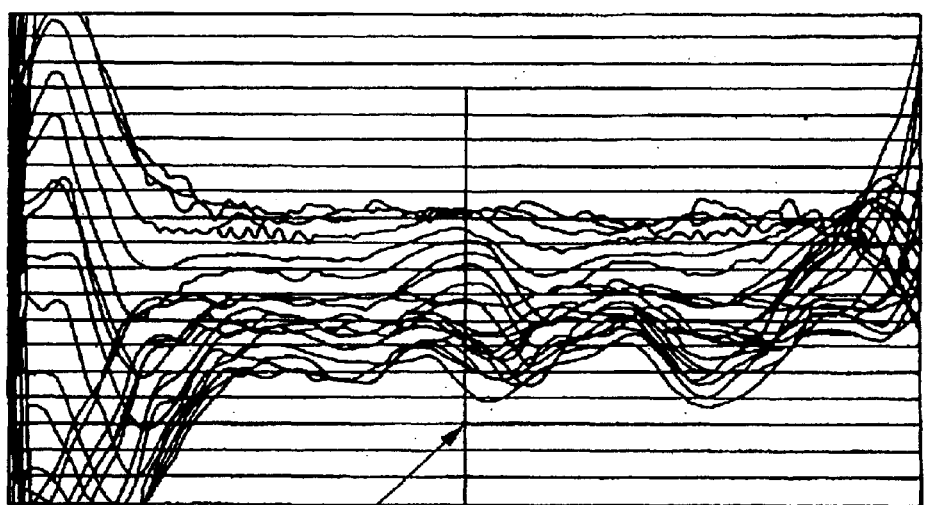
FIG. 10 is a graph showing detector trace plots produced in accordance with the invention for a plurality of driving frequencies.

FIG. 10 is a graph showing traces resulting from traversal of a pipe section selected from a plurality of different periodic driving frequencies extending over the range of 20 to 300 Hz, namely 24 different periodic driving frequencies. Where a graph showing a plurality of periodic driving frequencies is produced, it is preferable to select a frequency separation of each periodic driving frequency from another such that the range of frequencies extends at least over one octave and the individual frequencies are separated from each other by at least one eighth of an octave. For example, use of a range of at least 2 octaves will enable selection of about 17 frequencies, where each separated by one eighth of an octave. Wider separation of individual frequencies than one eighth of an octave will produce useful results but will reduce the number of frequency traces from 17 over the range. Conversely, narrower separation of individual frequencies than one eighth of an octave for each trace will increase the number of frequencies plotted from 17 over the range. However, the individual traces produced by the narrower separated individual frequencies may not provide significant additional differences to warrant use of such narrower selected frequency separation.

In the traces of the graph of FIG. 9, a wire break is manifested at 240, which show a plurality of signal trace or plots that have positive sloping and negative sloping excursions in the range of 240. Thus, there is a sign reversal in the slopes of the excursions of the various traces in the region of 204, which is indicative of the presence of a wire break at that location. When performing the test to produce data for production of the graphs, it is desirable to obtain test data points for a particular frequency at a particular location as quickly as possible. The less time taken to gather data for each data point, will increase the number data points available from a pipe inspection test session over a given time period.

Figure 11:
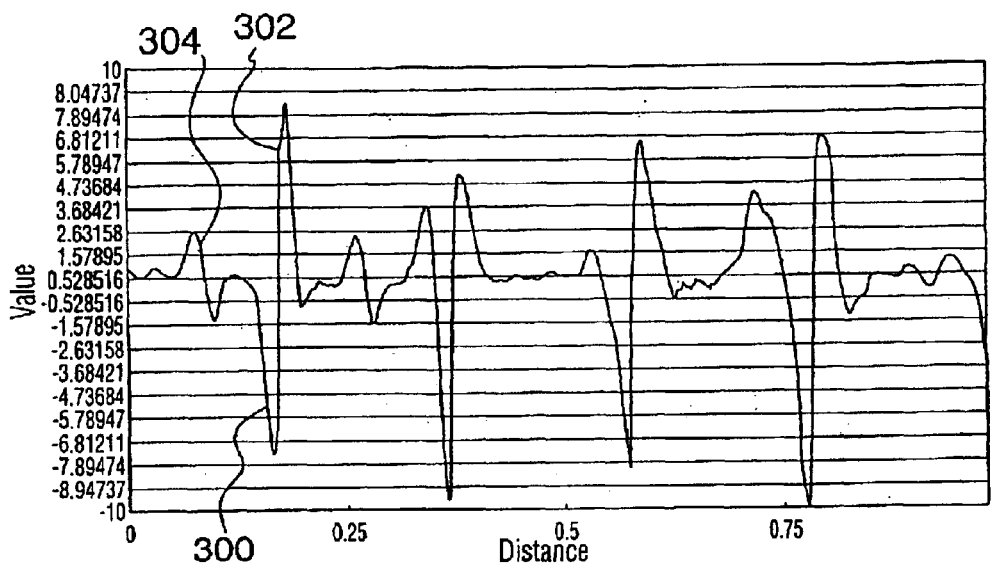
FIG. 11 is a graph showing a detector trace plot of a component of a detector output produced in accordance with the invention for a single driving frequency.

FIG. 11 is graph showing a plot of a component of a detector output produced by the apparatus of the invention for a single periodic driving frequency. The plot of FIG. 11 represents a trace produced at a single driving frequency over the traversal of the pipe under inspection. The plot shows the output of either an X or Y component of the output of LIA 219 as the vertical axis for locations along the pipe as the horizontal axis of the plot. Large excursions 300 and 302 occur where the detector apparatus of the invention crosses over a pipe joint. Relatively smaller excursions 304 are representative of an anomaly which may warrant further consideration, as will be described in more detail with reference to FIG. 12.

Figure 12:
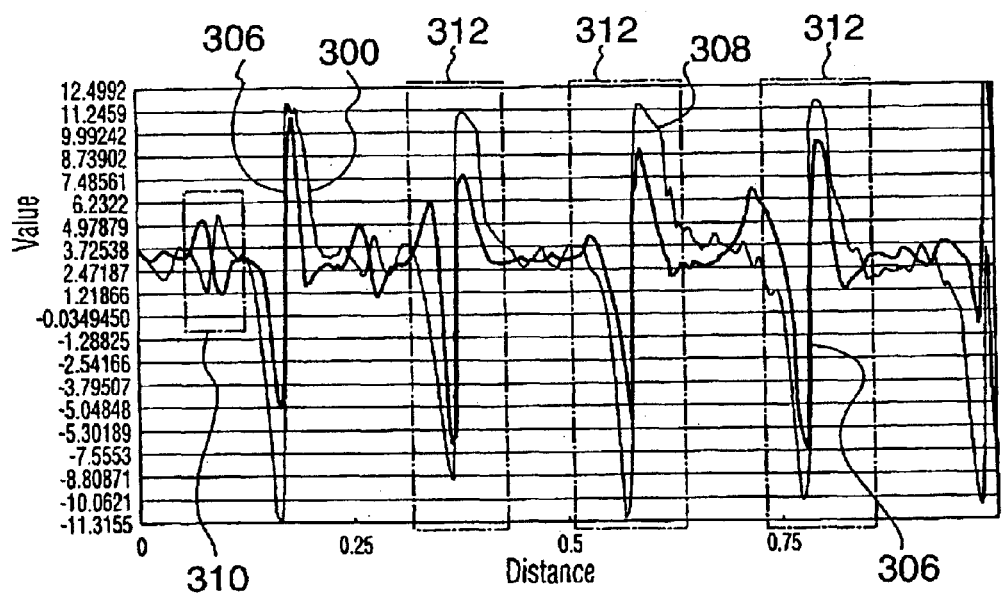
FIG. 12 is a graph showing a plot of a component of a detector output and a corresponding plot of a phase shifted component of a detector output produced in accordance with the invention for a single driving frequency.

FIG. 12 is graph showing a plot of a component of a detector output and a corresponding plot of a phase shifted component of a detector output produced by the apparatus of the invention for a single periodic driving frequencies. One plot of FIG. 11 is a plot of a component of a detector output 306 corresponding to the plot depicted in FIG. 11. The plot may be produced from either the X, or in-phase, component or the Y, or quadrature, component of the output of LIA 219 provided on lines 221 or 223 of FIG. 8. The corresponding outputs X or Y for the vector of the received signal are as described and shown with reference to FIG. 8a. The vector of the received signal may be transposed by an angle alpha, the process of which is described in more detail with reference to FIG. 13. Transposition of the component by an angle alpha results in a second plot 308 of the transposed corresponding component (which is either the in-phase or quadrature component). The angle of transposition, alpha, is selected to provide a slope reversal of an anomaly of interest as shown in the region of the plot at the area referenced by numeral 310. Production of the plot 308 based on transposition of the detector vector by the transposition angle alpha results in a mirror image form of plot only at the region of interest, namely region 310 which corresponds to an anomaly. The larger excursions occurring at known bell and spigot pipe joints at areas 312 of the plot do not provide a mirror image plot in the transposition plot as illustrated when referring the two plots 306 and 308 in the regions 312. Thus selection of the transposition angle alpha is made such that the known anomalies occurring at a bell and spigot pipe joint do not result in mirror image excursions between the recorded plot 306 and the transposed plot 308, calculated based on the transposition angle alpha.

Figure 13:
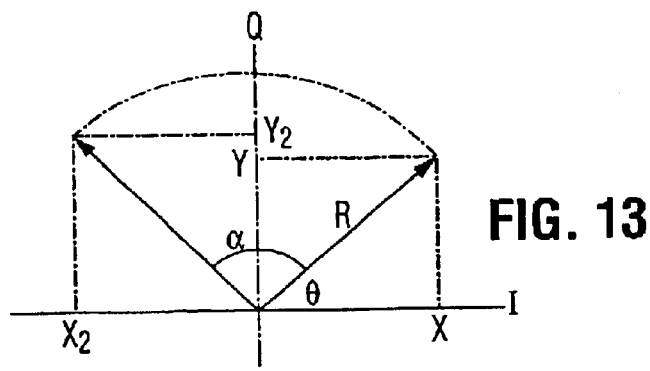
FIG. 13 is a graph of a vector output representing the in-phase and quadrature components of a received signal output from a lock-in amplifier transposed by an angle alpha.

FIG. 13 is a graph of a vector output representing the in-phase and quadrature components of a received signal output from a lock-in amplifier. The in-phase axis I has a component value X corresponding to the received vector and the quadrature axis Q has a component value Y corresponding to the received vector. The vector may be described in polar co-ordinates as having a length R and a phase theta relative to the driving frequency. The vector may be transposed by an angle alpha, which will cause the in-phase and quadrature components of the received vector to assume new values. FIG. 13 illustrates the transposition transformation of one vector or data point pair by an angle alpha. This transposition is performed against all logged data point pairs of a data set to produce the corresponding trace 308, which is transposed by an angle alpha as depicted in FIG. 12.

Figure 14A:
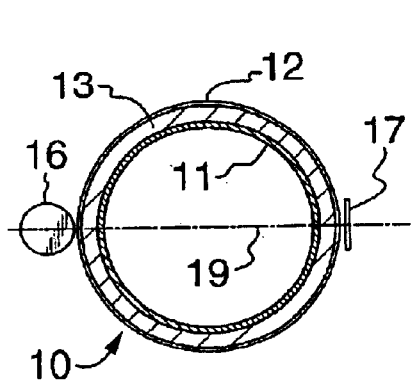
FIG. 14a is a cross section through a pre-stressed concrete pipe, showing schematically a preferred arrangement of the driver and detector around the pipe under test.

FIG. 14*a* is a cross section through a pre-stressed concrete pipe, generally indicated by 10, showing schematically a preferred arrangement of the driver and detector positioned exterior to, or around, the pipe under test. The pre-stressed concrete pipe typically has an inner metal cylinder 11. Depending upon the type and grade of pipe, either pre-stressing wires are wound directly onto the cylinder, or a layer of concrete 13 is cast onto the cylinder, and the pre-stressing wires 12 are wound on the layer of concrete. As noted previously, some pipes also have a layer of concrete cast inside the pipe, separating the metal cylinder from the interior volume of the pipe. Generally, another layer of concrete or protective mortar is cast around the wires to complete the pipe.

The pipe inspection apparatus is shown disposed on the exterior of the pipe and comprises a driver coil 17 and a detector 16. The detector is preferably a coil detector capable of detecting magnetically induced currents in the pipe under inspection. The detector is adapted to receive magnetic flux and convert it into a measurable electrical current and voltage. The detector 16 is placed proximal to the exterior surface of the pipe. It is preferred that the detector does not touch the pipe surface, as this would impede movement of the detector along the exterior surface of the wall. However, the gap between the detector 16 and wall of the pipe 10 should be kept as small as is conveniently possible, having regard for the fact that the detector is to be moved along the length of the pipe.

Figure 14B:
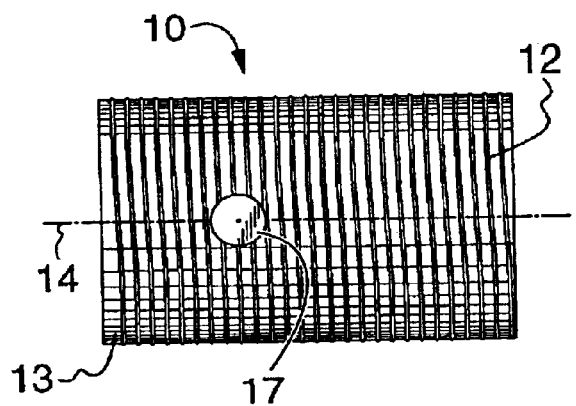
FIG. 14b is an elevation view of the pipe and arrangement of FIG. 14a, with the protective mortar of the pipe is not shown so that the underlying structure can be viewed.

Reference numeral 19 represents a diameter of the pipe, which passes through detector 16 in the arrangement of FIGS. 14*a* and 14*b*. In this arrangement, driver coil 17 is disposed at the opposite end of the diameter 19 from detector 16. The driver coil is driven with the same low frequency alternating current that has been previously described. As previously described, it is preferable that the driver be placed as close as conveniently possible to the wall of the pipe. Having regard to the fact that the apparatus will be moved along the pipe, it is not desirable to have the driver 17 dragging against the exterior wall of the pipe in operation of the apparatus.

FIG. 14*b* is an elevation view of the pipe and arrangement of FIG. 14*a*, where the protective mortar of the pipe is not shown so that it is possible to view the pre-stressing wires 12. For clarity, only a few representative wires are shown. The driver coil 17 is visible, but the detector coil 16 is obscured behind pipe 10.

Figure 15A:
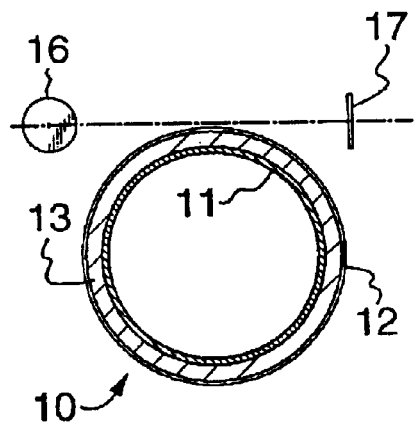

FIG. 15*a* is a cross section through a pre-stressed concrete pipe, showing schematically a alternate arrangement of the driver and detector around the pipe under test from the arrangement of FIG. 14*a*. The pipe inspection apparatus is shown disposed on the exterior of the pipe and comprises a driver coil 17 and a detector 16. Each of the driver 17 and the detector 16 is placed proximal to but not touching the exterior surface of the pipe as is driver coil 17. The driver and detector coils are positioned so that the axis of the pipe (see 14 of FIG. 15*b*) is normal to a line extending between the driver 17 and detector 16. As previously described, the driver coil is driven with a low frequency alternating current.

Figure 15B:
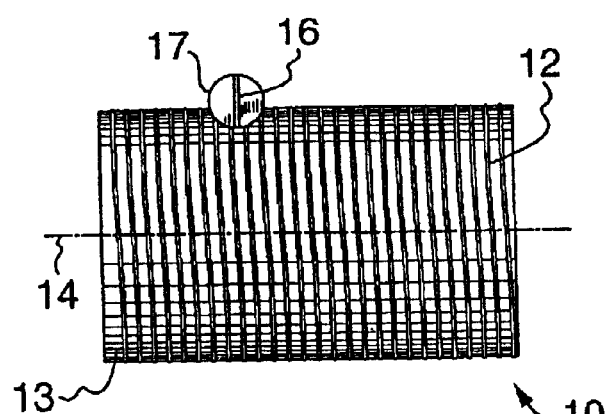
FIG. 15b is an elevation view of the pipe and arrangement of FIG. 15a, where the protective mortar of the pipe is not shown so that the underlying structure can be viewed.

FIG. 15*b* is an elevation view of the pipe and arrangement of FIG. 15*a*, in which the protective mortar of the pipe is not shown to enable viewing of the pre-stressing wires 12. For clarity, only a few representative wires are shown.

Figure 16:
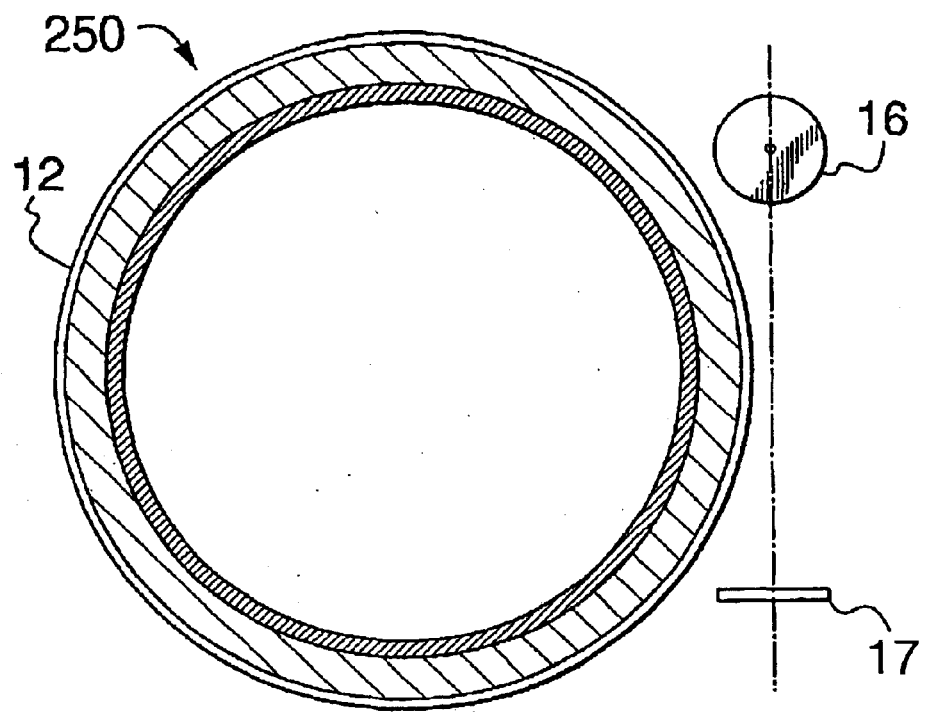
FIG. 16 is a top view of a pre-stressed water reservoir vessel, showing schematically an arrangement of the driver and detector around the vessel under test.

FIG. 16 is a top view of a pre-stressed water reservoir vessel 250, showing schematically an arrangement of the driver and detector around the vessel under test. The inspection apparatus is shown disposed on the exterior of the reservoir vessel 250 and comprises a driver coil 17 and a detector 16. Each of the driver 17 and the detector 16 is placed proximal to but preferably not touching the exterior surface of the reservoir vessel 250 as is driver coil 17. The driver and detector coils are positioned so that the axis of the reservoir vessel (see 14 of FIG. 15*b*) is normal to a line, shown in FIG. 16, extending between the driver 17 and detector 16. As previously described, the driver coil is driven with a low frequency alternating current. In operation of the arrangement of FIG. 16, the driver and detector are maintained in a spaced relationship and the apparatus is moved along the axis of the water reservoir vessel 250. Multiple passes of the vessel can be performed using a number of inspection processes. The apparatus can traverse the water reservoir vessel under test. With each test, the distance between the driver 17 and the detector 16 can be changed, or the radial location of driver and detector apparatus around the perimeter of the water reservoir can be changed. Another variation is to provide the driver at a fixed location and extend the receiver along a line of the perimeter of the water reservoir oriented parallel to the axis of the water reservoir.

Figure 17:
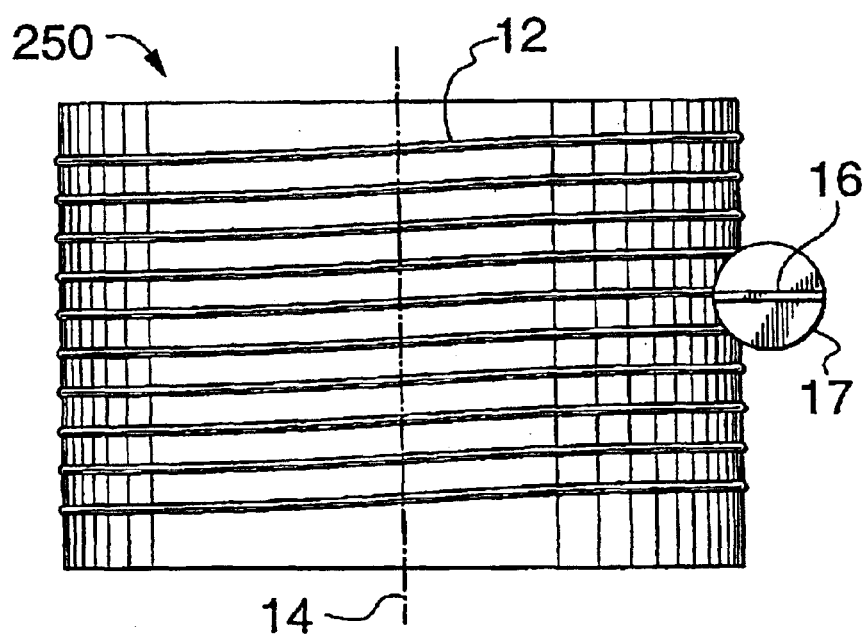
FIG. 17 is an elevation of the vessel and arrangement of FIG. 16.

FIG. 17 is an elevation of the vessel and arrangement of FIG. 16 with the pre-stressing wires 12 exposed for clarity.

FIGS. 18*a*, 18*b*, 18*c* and 18*d* are cross sections through a pre-stressed concrete cylinder showing schematically alternate preferred arrangements of the driver and detector disposed about the cylinder under test. In these embodiments, the driver and detector are disposed on opposite sides of a cylinder under test. The arrangement of apparatus of FIGS. 18*a* through 18*d* are less preferred as maintaining the orientation and relative position of the detector to driver as the apparatus extends along the cylinder under test is required. In the arrangement of each of FIGS. 18*a* through 18*d*, the inspection apparatus, comprising a driver coil 17 and a detector 16, is shown disposed on proximal to but not touching a surface of the cylinder 10 to allow movement of the apparatus along the surface of the cylinder.

Figure 18A:
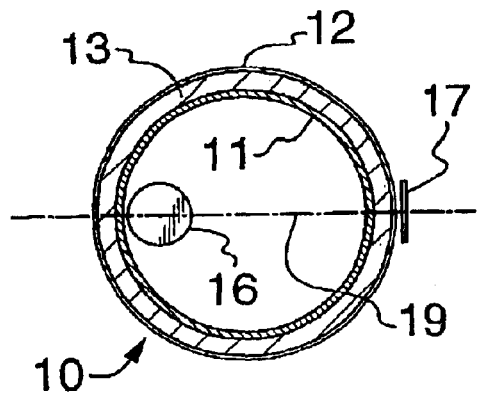
FIGS. 18a, 18b, 18c and 18d are cross sections through a pre-stressed concrete pipe, showing schematically alternate preferred arrangements of the driver and detector disposed about a pipe under test.

In FIG. 18*a*, reference numeral 19 represents a diameter of the cylinder, which is parallel to the axis of driver 17 and passes through detector 16. In this arrangement, driver coil 17 is disposed on the exterior of cylinder 10 along the diameter 19 from detector 16, which is disposed on an interior side of cylinder 10.

Figure 18B:
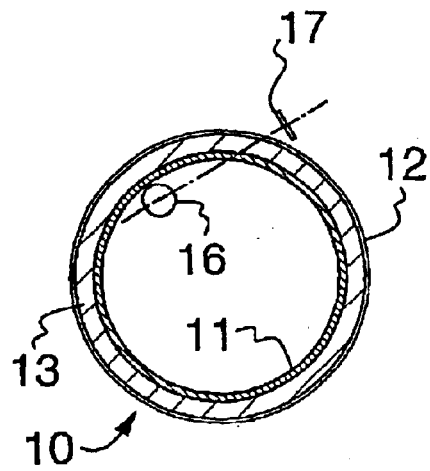

In FIG. 18*b*, driver 17 is disposed on the exterior side of cylinder 10 under test. The axis of driver 17 is oriented toward detector 16 such that the line extending between the driver 17 and detector 16 is normal or orthogonal to the axis of the cylinder under inspection. In this arrangement, driver coil 17 is disposed on the exterior of cylinder 10 and detector 16 is disposed on an interior side of cylinder 10.

Figure 18C:
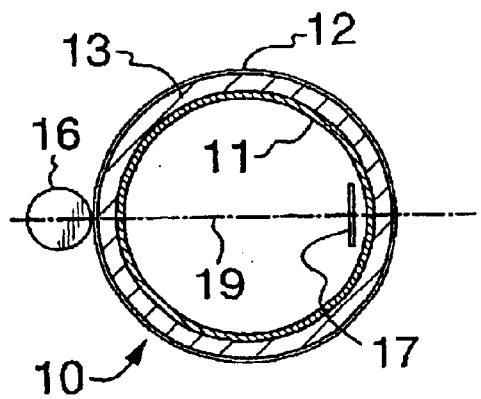

In FIG. 18*c*, reference numeral 19 represents a diameter of the cylinder, which is parallel to the axis of driver 17 and passes through detector 16. In this arrangement, driver coil 17 is disposed on the interior of cylinder 10 along the diameter 19 from detector 16, which is disposed on the exterior side of cylinder 10.

Figure 18D:
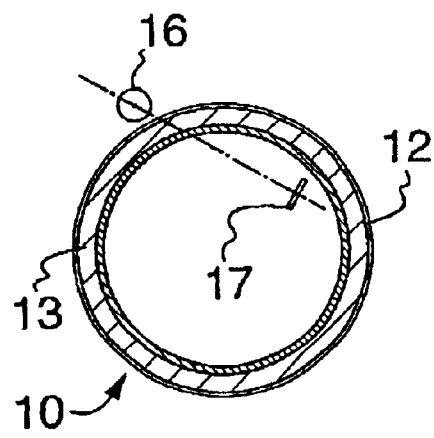

In FIG. 18d, driver 17 is disposed on an interior side of cylinder 10 under test. The axis of driver 17 is oriented toward detector 16 such that the line extending between the driver 17 and detector 16 is normal or orthogonal to the axis of the cylinder under inspection. In this arrangement, driver coil 17 is disposed on an interior side of cylinder 10 and detector 16 is disposed on an exterior side of cylinder 10. The line extending between driver 17 and detector 16 is normal or orthogonal to the axis of the cylinder 10 under test.

While the invention has been shown with respect to certain embodiments, it will be understood that many variations to such embodiments will be evident to a person skilled in the art, and it is intended that all such evident variations should be protected.

We claim:

1. A method of detecting discontinuities in tensioning wires or a concrete pipe comprising:
   (i) providing a driving signal to a driver having an axis oriented orthogonal to an axis of a concrete pipe and proximal to an inside surface thereof to generate an induced current in pre-stressing elements extending substantially circumferentially of the pipe;
   (ii) providing a detector for producing an output responsive to a magnetic flux, the detector located in dose proximity to an interior wall of a pipe and axially displaced not more than one pipe diameter of a plane orthogonal to the axis of the pipe and common to the driver,
   (iii) moving the detector along the wall of the pipe; and
   (iv) recording the output and the location of the detector as it moves.

2. A method of testing tensioning wires of a pre-stressed concrete pipe along a length thereof using apparatus including magnetic flux production means and magnetic flux detector means each disposed proximal to a surface of a pipe to be tested in a spaced relationship to the other and axially disposed within one pipe diameter to the other, the magnetic flux production means producing a magnetic field in response to a driving signal and the detector means producing a detector signal in response to magnetic flux, location indication means and control means operatively connected to said location indication means, to said magnetic flux means and to said detector means, the method comprising:
   (i) providing a driving signal of at least one frequency;
   (ii) receiving a detector signal;
   (iii) producing an output representative of the detector signal corresponding to the in-phase and quadrature components, of the detector signal in relation to a frequency of the driving signal; and
   (iv) recording said output representative of the detector signal and a location indication;
   whereby at least one fundamental frequency is recorded over a range of locations traversed along a length of pipe.

3. The method of claim 2 including the step of producing an output representative of the amplitude and the phase of the detector signal expressed in Cartesian co-ordinates.

4. The method of claim 2 wherein for each frequency of the driving signal, a range of locations are displayed.

5. The method of claim 2 wherein the length along the pre-stressed concrete pipe is a range of locations defined by a start location and an end location and the pipe is traversed from the start location to the end location for each selected frequency.

6. The method of claim 2 further includes the steps of displaying a first trace for at least one selected frequency of the recorded detector signal and the selected location upon a display means and displaying a second trace calculated from the Cartesian co-ordinates of the first trace based on a transposition angle alpha.

7. The method of claim 6 wherein the transposition angle alpha is selected to produce a mirror image excursion of portions of each trace over a range of interest.

8. The method of claim 7 wherein the display means is a display device.

9. The method of claim 7 wherein the display means is a printed graph.

10. A method of detecting discontinuities in tensioning wires of a concrete cylinder comprising:
    (i) providing a driving signal to a driver coil means having an axis oriented orthogonal to an axis of a concrete cylinder to generate induced current in pre-stressing elements extending substantially circumferentially around the cylinder;
    (ii) providing a detector proximal to a surface of the concrete cylinder and spacedly disposed from said driver means along said axis of said driver coil means, the detector to produce an output responsive to a magnetic flux;
    (iii) filtering the output of the detector relative to the driving signal; and
    (iv) recording the filtered output and the location of the detector.

11. A method of testing the tensioning wires of a pre-stressed concrete cylinder along a length thereof using apparatus including magnetic flux production means and magnetic flux detector means each disposed proximal to a surface of the cylinder in a spaced relationship to the other and axially disposed not more than one cylinder diameter from the other, the magnetic flux production means for producing a magnetic field in response to a driving signal and the detector means for producing a detector signal in response to magnetic flux, location indication means and control means operatively connected to said location indication means, to said magnetic flux means and to said detector means, the method comprising:
    (i) providing a driving signal of at least one frequency;
    (ii) receiving a detector signal;
    (iii) producing an output representative of the detector signal corresponding to the in-phase and quadrature components of the detector signal in relation to the fundamental frequency of the driving signal; and
    (iv) recording the output representative of the detector signal in relation to the fundamental frequency, the fundamental frequency and the location;
    whereby at least one fundamental frequency is recorded over a range of locations traversed along a length of cylinder.

12. The method of claim 11 wherein the step of producing an output representative of the amplitude and the phase of the detector signal comprises forming Cartesian co-ordinates X and Y.

13. The method of claim 11 wherein for each frequency of the driving signal, a range of locations are displayed.

14. The method of claim 11 wherein the length along the pre-stressed concrete cylinder is a range of locations defined by a start location and an end location and the cylinder is traversed from the start location to the end location for each selected frequency.

15. The method of claim 11 further including the steps of displaying a first trace for at least one selected frequency of the recorded detector signal and the selected location upon a display means and displaying a second trace calculated from either the X or Y co-ordinates of the first trace based on a transposition angle alpha.

16. The method of claim 15 wherein the transposition angle alpha is selected to produce a mirror image excursion of portions of each trace over a range of interest.

17. The method of claim 16 wherein the display means is a display device.

18. The method of claim 16 wherein the display means is a printed graph.

19. A method of testing the tension wires of a pre-stressed concrete cylinder along a length thereof using apparatus including magnetic flux production means and magnetic flux detector means each disposed proximal to a surface of the cylinder, the magnetic flux production means for producing a magnetic field in response, to a driving signal and the detector means for producing a detector signal in response to magnetic flux, location indication means and control means operatively connected to said location indication means, to said magnetic flux means and to said detector means, the method comprising:

(i) providing a driving signal of at least one frequency (ii) positioning the detector means in relation to the magnetic flux production means, each said detector means and the magnetic flux production means axially disposed not more than one cylinder diameter to the other;

(iii) receiving a detector signal;

(iv) producing an output representative of the detector signal corresponding to the in-phase and quadrature components of the detector signal in relation to the fundamental frequency of the driving signal; and (v) recording the location of the detector means end output representative of the detector signal in relation to the fundamental frequency, the fundamental frequency and the location of a deter;

whereby at least one fundamental frequency is recorded over a range of locations traversed by said detector means along a length of a pre-stressed concrete cylinder.

20. The method of claim 19 wherein producing an output representative of the amplitude and the phase of the detector signal comprises Cartesian co-ordinates X and Y.

21. The method of claim 19 wherein for each frequency of the diving signal, a range of locations of said detector means with respect to the axis of the concrete cylinder are displayed.

22. The method of claim 19 wherein the length along the pre-stressed concrete cylinder is a range of locations defined by a start location and an end location and the cylinder is traversed by said detector means from the start location to the end location for each selected frequency.

23. The method of claim 19 further includes the steps of producing a first trace for at least one selected frequency of the recorded detector signal and the selected location upon a display means and producing a second trace calculated from either the X or Y co-ordinates of the first trace based on a transposition angle alpha.

24. The method of claim 23 wherein the transposition angle alpha is selected to produce a mirror image excursion of portions of each trace over a range of interest.

25. The method of claim 24 wherein the display means is a display device.

26. The method of claim 24 wherein the display means is a printed graph.

27. A method of detecting discontinuities in spirally wound metallic pre-stressing elements of a concrete pipe having such elements which comprises:

(i) providing a detector coil which has its axis parallel to the axis of the pipe, and which is of a diameter less than one quarter of the diameter of the pipe, (ii) placing the detector coil in close proximity to the interior wall of the pipe, (iii) generating a periodically varying induced current in the pre-stressing elements by a driver coil orthogonal to the detector coil;

(iv) moving the detector coil along the wall of the pipe; and (v) recording the distance moved or the location of the detector coil, and the induced voltage or current sensed by the detector coil as it moves.

28. A method as claimed claim 27 in which the periodic current is a sinusoidal waveform.

29. A method as claimed in claim 27 in which the periodic current has a sawtooth waveform.

30. A method as claimed in claim 27 in which the periodic current has a square waveform.

* * * * *

UNITED STATES PATENT AND TRADEMARK OFFICE
CERTIFICATE OF CORRECTION

PATENT NO. : 6,781,369 B2
DATED : August 24, 2004
INVENTOR(S) : Paulson et al.

It is certified that error appears in the above-identified patent and that said Letters Patent is hereby corrected as shown below:

Column 21,
Line 21, change "or" to -- of --;
Line 29, change "dose" to -- close --;

Column 23,
Line 39, change "end" to -- and --;
Line 42, change "deter" to -- detector --.

Signed and Sealed this

Twenty-second Day of February, 2005

JON W. DUDAS
*Director of the United States Patent and Trademark Office*